United States Patent
Regev et al.

(10) Patent No.: US 11,841,371 B2
(45) Date of Patent: Dec. 12, 2023

(54) PROTEOMICS AND SPATIAL PATTERNING USING ANTENNA NETWORKS

(71) Applicants: The Broad Institute, Inc., Cambridge, MA (US); Massachusetts Institute of Technology, Cambridge, MA (US)

(72) Inventors: Aviv Regev, Cambridge, MA (US); Jellert Gaublomme, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 765 days.

(21) Appl. No.: 16/352,355

(22) Filed: Mar. 13, 2019

(65) Prior Publication Data

US 2019/0285644 A1 Sep. 19, 2019

Related U.S. Application Data

(60) Provisional application No. 62/642,422, filed on Mar. 13, 2018.

(51) Int. Cl.
| | | |
|---|---|---|
| *G01N 33/68* | (2006.01) | |
| *C12N 15/10* | (2006.01) | |
| *C12N 15/11* | (2006.01) | |
| *C40B 40/06* | (2006.01) | |

(52) U.S. Cl.
CPC ..... *G01N 33/6842* (2013.01); *C12N 15/1065* (2013.01); *C12N 15/1093* (2013.01); *C12N 15/11* (2013.01); *C40B 40/06* (2013.01); *G01N 33/6818* (2013.01)

(58) Field of Classification Search
None
See application file for complete search history.

(56) References Cited

U.S. PATENT DOCUMENTS

| | | | |
|---|---|---|---|
| 5,580,737 | A | 12/1996 | Polisky et al. |
| 5,660,985 | A | 8/1997 | Pieken et al. |
| 7,708,949 | B2 | 5/2010 | Stone et al. |
| 8,337,778 | B2 | 12/2012 | Stone et al. |
| 8,765,485 | B2 | 7/2014 | Link et al. |
| 9,364,803 | B2 | 6/2016 | Yurkovetsky et al. |
| 2006/0163385 | A1 | 7/2006 | Link et al. |
| 2007/0003442 | A1 | 1/2007 | Link et al. |
| 2007/0184489 | A1 | 8/2007 | Griffiths et al. |
| 2007/0195127 | A1 | 8/2007 | Ahn et al. |
| 2008/0003142 | A1 | 1/2008 | Link et al. |
| 2008/0014589 | A1 | 1/2008 | Link et al. |
| 2009/0005254 | A1 | 1/2009 | Griffiths et al. |
| 2009/0131543 | A1 | 5/2009 | Weitz et al. |
| 2010/0136544 | A1 | 6/2010 | Agresti et al. |
| 2010/0137163 | A1 | 6/2010 | Link et al. |
| 2012/0219947 | A1 | 8/2012 | Yurkovetsky et al. |
| 2014/0199730 | A1 | 7/2014 | Agresti et al. |
| 2014/0199731 | A1 | 7/2014 | Agresti et al. |
| 2014/0256595 | A1 | 9/2014 | Link et al. |
| 2015/0051113 | A1* | 2/2015 | Kim ..... C12N 15/1093 435/6.12 |
| 2016/0060691 | A1 | 3/2016 | Giresi et al. |
| 2016/0208323 | A1 | 7/2016 | Bernstein et al. |
| 2018/0010174 | A1 | 1/2018 | Schaus et al. |
| 2020/0248176 | A1* | 8/2020 | Belhocine ..... C12N 15/1075 |

FOREIGN PATENT DOCUMENTS

| | | |
|---|---|---|
| WO | 01/89788 A2 | 11/2001 |
| WO | 2004/002627 A2 | 1/2004 |
| WO | 2004/091763 A2 | 10/2004 |
| WO | 2005/021151 A1 | 3/2005 |
| WO | 2006/040551 A2 | 4/2006 |
| WO | 2006/040554 A1 | 4/2006 |
| WO | 2006/096571 A2 | 9/2006 |
| WO | 2007/081385 A2 | 7/2007 |
| WO | 2007/089541 A2 | 8/2007 |
| WO | 2007/133710 A2 | 11/2007 |
| WO | 2008/063227 A2 | 5/2008 |
| WO | 2009/012418 A2 | 1/2009 |
| WO | 2011/079176 A2 | 6/2011 |
| WO | 2014/047556 A1 | 3/2014 |
| WO | 2014/047561 A1 | 3/2014 |
| WO | 2014/085802 A1 | 6/2014 |
| WO | 2014/143158 A1 | 9/2014 |
| WO | 2014/210353 A2 | 12/2014 |
| WO | 2015/164212 A1 | 10/2015 |
| WO | 2016/040476 A1 | 3/2016 |
| WO | 2016/100976 A2 | 6/2016 |
| WO | 2016/168584 A1 | 10/2016 |
| WO | 2017/075265 A1 | 5/2017 |
| WO | 2017/075292 A1 | 5/2017 |

(Continued)

OTHER PUBLICATIONS

Riccelli et al. (Nucleic Acids Research 29:99-1004) (Year: 2001).*
Wardle et al. (Nucleic Acids Research 36:705-11) (Year: 2008).*
Schaus et al., "A DNA Nanoscope via Auto-Cycling Proximity Recording", Nature Communications, vol. 8, No. 1, Sep. 25, 2017, 9 pages.
Stoeckius et al., "Simultaneous Epitope and Transcriptome Measurement in Single Cells", Nature Methods, vol. 14, Jul. 31, 2017, 10 pages.

*Primary Examiner* — Christopher M Gross
(74) *Attorney, Agent, or Firm* — F. Brent Nix, Esq.; Johnson, Marcou, Isaacs & Nix, LLC; Michael B. Scher, Esq.

(57) ABSTRACT

The application relates to methods and systems for proteomics and spatial mapping of biomolecules using a next generation sequencing readout to decipher biomolecular and cellular interaction networks. Specifically, disclosed are antenna networks generated by conjugating DNA antennas to proteins. The antennas carry a unique antenna identifier (UAI) sequence that can provide spatial location of the network, as well as biomolecules by transfer of the UAI to reporter oligonucleotides associated with other antennas and biomolecules. The methods and systems are also applicable to single cells.

26 Claims, 5 Drawing Sheets

(56) References Cited

FOREIGN PATENT DOCUMENTS

| WO | 2017/075294 A1 | 5/2017 |
| WO | 2017/156336 A1 | 9/2017 |
| WO | 2017/164936 A1 | 9/2017 |

\* cited by examiner

PROTEOMICS AND SPATIAL PATTERNING USING ANTENNA NETWORKS

CROSS-REFERENCE TO RELATED APPLICATIONS

This application claims the benefit of U.S. Provisional Application No. 62/642,422, filed Mar. 13, 2018. The entire contents of the above-identified application are hereby fully incorporated herein by reference.

This invention was made with government support under grant number HG006193 awarded by National Institutes of Health. The government has certain rights in the invention.

TECHNICAL FIELD

The subject matter disclosed herein is generally directed to methods and systems for proteomics using a sequencing readout. Additionally, the subject matter is directed to methods and systems for single-cell proteomics. Furthermore, the subject matter is directed to methods and systems for mapping spatial locations of biomolecules, such as proteins and protein complexes in the context of membrane or chromatin location. The methods and systems also allow for measuring protein abundance and mRNA abundance.

BACKGROUND

A cell's phenotype is characterized by the interplay of its internal state and the environmental signals it receives. It is becoming increasingly clear that to thoroughly understand cellular phenotype multi-omic measurements of single cells is necessary. Further, it is important to evaluate single cells in a tissue context. To date, single-cell genomics studies have primarily focused on characterizing the internal state by mRNA abundance. Proteome profiling of single cells has been restricted to only a handful of proteins due to limits of spectral overlap of fluorescent tags for flow cytometry (Perfetto, et al., (2004) Nature reviews Immunology 4, 648-655) or available isotope tags for mass cytometry (Bendall, et al. (2011) Science 332, 687-696), severely limiting our ability to map a pathway extensively. Present high multiplex readouts typically require large amounts of cells as input, thereby ignoring cellular heterogeneity and reflecting cumulated potential pathway behaviors, complicating interpretation of pathway mechanisms. For example, mass spectrometry (LC-MS/MS) allows quantitative analysis of entire proteomes, but deep analysis requires large amounts of protein/cells, and is limited in throughput (i.e. amount of cells that can be analyzed over a given time period). Moreover, most single-cell proteomic assays are agnostic to protein complex compositions, and are incompatible with simultaneous RNA readout. Similarly, tissue level biology has typically been studied by histology or immunohistochemistry, both of which only allow visualization of a handful of predetermined parameters, limiting our potential to discover novel biology in situ. Thus, there is a need to quantify protein abundances, modifications and interactions, and decipher how these factors dynamically inform transcriptional and epigenetic responses.

Citation or identification of any document in this application is not an admission that such document is available as prior art to the present invention.

SUMMARY

In certain example embodiments, the present invention provides for novel methods and systems for quantifying protein abundances, protein modifications and protein interactions. In further embodiments, the present invention provides for novel methods and systems for determining spatial patterning of proteins and/or protein modifications. In further embodiments, the present invention provides for novel methods and systems for determining spatial patterning of proteins and/or protein modifications over the genome of a cell. The systems and methods disclosed herein can also be applied to single-cell technologies.

In one aspect, the present invention provides for a library of antenna oligonucleotides, each antenna oligonucleotide comprising: a partially-double-stranded hairpin structure having a loop region and a single-stranded 3' end; a primer-binding sequence at the 3' end of the hairpin structure; a sequence 5' of the primer-binding sequence comprising a unique antenna identifier (UAI) sequence, wherein the UAI sequence is part of or partially part of the single-stranded 3' end or is part of the double-stranded region, and wherein each antenna has a unique UAI sequence; a double-stranded sequence comprising a universal hybridization sequence; a double-stranded palindromic sequence; a modification that terminates polymerization between the palindromic sequence and the loop region of the hairpin; and a binding moiety on the loop region for labeling biological modules. In certain embodiments, the antenna oligonucleotide comprises from 5' to 3' a universal hybridization sequence, palindromic sequence, a modification that terminates polymerization, stem loop sequence, a modification that terminates polymerization, palindromic sequence, a universal hybridization complementary sequence, UAI sequence and primer-binding sequence. The single-stranded sequence may comprise a modification before the double-stranded region of the hairpin structure that weakens DNA hybridization after primer binding to the primer-binding sequence and extension of the primer. The modification may comprise a bulge nucleotide or a phosphorothioate modification. Alternatively, primers specific to the primer-binding sequence may comprise the modification, thus the antenna oligonucleotides would not require the modification. The binding moiety may comprise a biotin molecule or a Click chemistry moiety. The modification that terminates polymerization may comprise a non-DNA spacer or an Iso-dC/dG pair.

In another aspect, the present invention provides for a method of mapping the proximity between biomolecules in discrete biological modules comprising: modifying a biological sample comprising one or more biological modules with protein linker molecules, wherein the protein linker molecules are linked to proteins in the one or more biological modules; labeling the modified biological sample with one or more affinity ligands specific for a biomolecule, wherein the one or more affinity ligands are linked to an ABC oligonucleotide comprising an antibody barcode (ABC) specific for each affinity ligand and a universal hybridization sequence; establishing an antenna network comprising linking antenna oligonucleotides to the protein linker molecules, wherein each antenna oligonucleotide comprises: a partially-double-stranded hairpin structure having a loop region and a single-stranded 3' end, a primer-binding sequence at the 3' end of the hairpin structure, a sequence 5' of the primer-binding sequence comprising a unique antenna identifier (UAI) sequence, wherein the UAI sequence is part of or partially part of the single-stranded 3' end or is part of the double-stranded region, and wherein each antenna has a unique UAI sequence, a double-stranded sequence comprising a complementary universal hybridization sequence, a double-stranded palindromic sequence, a modification that terminates polymerization between the palindromic sequence and the loop region of the hairpin, and a binding moiety on the loop region capable of being linked to the protein linker molecule; and incubating the sample with extension reagents and primers complementary to the primer-binding sequence under isothermal conditions, wherein the primers are extended to generate a free 3' tail comprising the palindromic sequence and hybridization sequence, whereby the free 3' tail is capable of hybridizing to another antenna oligonucleotide in proximity to generate a reporter molecule comprising two UAIs when extended and whereby the free 3' tail is capable of hybridizing to an ABC oligonucleotide in proximity to generate a UAI-ABC reporter molecule when extended; and sequencing the oligonucleotides present in the sample, whereby proximity recording to a specific antenna in the network. The single-stranded sequence may comprise a modification before the double-stranded region of the hairpin structure that weakens DNA hybridization after extension of the primer on the primer-binding sequence. The primer sequence may comprise a modification that weakens DNA hybridization after extension of the primer on the primer-binding sequence. The modification may comprise a bulge nucleotide or a phosphorothioate modification. The modification that terminates polymerization may comprise a non-DNA spacer or an Iso-dC/dG pair. The extension reagents may comprise a strand displacement polymerase.

In certain embodiments, the biological module comprises a protein complex. The protein complex may comprise nucleic acids. The nucleic acid may comprise genomic DNA.

In certain embodiments, the biological module comprises a cell, population of cells, organelle, or exosome. The population of cells may be a small population of interacting cells. In certain embodiments, the biological module is a tissue sample. In certain embodiments, the affinity ligands are specific for membrane proteins. Thus, the proximity of membrane proteins on the surface of cells may be mapped.

In certain embodiments, the ABC oligonucleotide further comprises a unique molecular identifier (UMI). In certain embodiments, the affinity ligands are antibodies, antibody fragments or aptamers.

In certain embodiments, the distance over which DNA proximity occurs is about 6-40 nM. The distance over which DNA proximity occurs can be adjusted based on modifying the length of the free 3' tail generated by the antenna molecule. The distance can be modified based on increasing or decreasing the length of the sequence between the modification in the single-stranded sequence and the modification that terminates polymerization. In other words, extension of the primer is terminated at the modification that terminates polymerization. Since there is a modification in the single-stranded sequence, the extended primer is then partially displaced by the original strand because of the modification in the single-stranded sequence. Thus, the free 3' tail is about the length between the termination modification and modification in the single-stranded sequence (preferably directly before double-stranded region, see, e.g., examples). Two antenna molecules or an antenna molecule and a biomolecule are considered to be "proximate" to each other if the distance between the two molecules is 0 nM to 100 nM. For example, the distance between two molecules proximate to each other may be 0 nM to 5 nM, 0 nM to 10 nM, 0 nM to 20 nM, 0 nM to 30 nM, 0 nM to 40 nM, or 0 nM to 50 nM. In preferred embodiments, the distance between two molecules proximate to each other may be 6 to 40 nM.

In certain embodiments, the one or more biological modules are fixed (e.g., in a hydrogel, or by a crosslinking agent, such as an aldehyde).

In certain embodiments, the protein linker molecules comprise biotin or click-chemistry moieties. Linking antenna oligonucleotides to the protein linker molecules may comprise binding biotin linked antenna oligonucleotides to biotin linker molecules via avidin molecules (e.g., a biotin avidin sandwich). Linking antenna oligonucleotides to the protein linker molecules may comprise binding antenna oligonucleotides to the linker molecules via click-chemistry.

In certain embodiments, before the step of modifying a biological sample the method may further comprise tagmentation of genomic DNA present in the biological sample with adaptors configured for hybridizing to the antenna oligonucleotides and extending the UAI sequence, whereby a UAI in proximity to the genomic DNA is transferred to the adaptor. Thus, sequencing of the UAI, adaptor and genomic DNA sequence can identify the genomic DNA in proximity to the antenna molecule. In certain embodiments, the one or more affinity ligands may comprise affinity ligands specific for histone modifications, whereby chromatin modifications may be mapped to genomic loci. In certain embodiments, given the close proximity of different modifications (e.g., steric hinderance), the method may comprise staining with affinity ligands in sets of 1 to 4 modifications, proximity recording, eluting off affinity ligands, and staining with a new set of 1 to 4 affinity ligands targeting different modifications. The histone modification may be selected from the group consisting of H2B Ser 14 (Phos), H3 Ser 10 (Phos), H3 Lys 9 (Me), H3 Lys 27 (Me), H3 Lys 36 (Me), H3 Lys 79 (Me), H4 Lys 20 (Me), H3 Lys 4 (Me), H3 Lys 9 (Ac), H3 Lys 14 (Ac), H3 Lys 23 (Ac), H4 arg 3 (Me), H3 Lys 27 (Ac), H4 arg 3 (Me), H4 lys 5 (Ac), H4 Ser 2 (phos), H4 Arg 3 (me), H4 Lys 5 (Ac) and H3 Lys 18 (Ac).

In certain embodiments, before the step of modifying a biological sample the method may further comprise: segregating single cells into discrete volumes; and covalently labeling proteins from single cells with protein labeling oligonucleotides, said oligonucleotides comprising cell of origin barcodes and a sequence configured for hybridizing to the antenna oligonucleotides and extending the UAI sequence, whereby the UAIs in proximity to proteins from a single cell can be identified by sequencing. The method may further comprise tagmentation of genomic DNA in the discrete volumes with adaptors configured for hybridizing to the antenna oligonucleotides and optionally comprising the cell of origin barcode. The method may further comprise capturing mRNA on capture oligonucleotides in the discrete volumes, said oligonucleotides comprising poly dT, the cell of origin barcodes for the discrete volume, and optionally a UMI. The discrete volumes may comprise droplets, microfluidic chambers, or microwells.

In certain embodiments, the discrete volumes are droplets comprising beads labeled with the protein labeling oligonucleotides. The beads may be further labeled with the mRNA capture oligonucleotides. The protein labeling oligonucleotides may be cleavable. The mRNA capture oligonucleotides may be cleavable. The oligonucleotides may be chemically-cleavable, enzymatically cleavable, or photo-cleavable.

In another aspect, the present invention provides for a system for mapping the proximity between biomolecules in discrete biological modules comprising: a plurality of antenna oligonucleotides configured for labeling biomolecules, said antenna oligonucleotides comprising: a partially-double-stranded hairpin structure having a loop region and a single-stranded 3' end, a primer-binding sequence at the 3' end of the hairpin structure, a sequence 5' of the primer-binding sequence comprising a unique antenna identifier (UAI) sequence, wherein the UAI sequence is part of or partially part of the single-stranded 3' end or is part of the double-stranded region, and wherein each antenna has a unique UAI sequence, a double-stranded sequence comprising a complementary universal hybridization sequence, a double-stranded palindromic sequence, a modification that terminates polymerization between the palindromic sequence and the loop region of the hairpin, and a binding moiety on the loop region capable of being linked to a protein; and one or more affinity ligands specific for a biomolecule, wherein the one or more affinity ligands are linked to an ABC oligonucleotide comprising an antibody barcode (ABC), wherein each ABC oligonucleotide is configured for hybridizing to the antenna oligonucleotides and extending the UAI sequence; primers complementary to the primer-binding sequence; and isothermal extension reagents.

In certain embodiments, the system further comprises a transposase loaded with tagmentation adaptors configured for hybridizing to the antenna oligonucleotides and extending the UAI sequence.

In certain embodiments, the system further comprises beads labeled with protein labeling oligonucleotides configured for labeling proteins, said oligonucleotides comprising cell of origin barcodes specific for each bead and a sequence configured for hybridizing to the antenna oligonucleotides and extending the UAI sequence. The beads may be further labeled with mRNA capture oligonucleotides, said oligonucleotides comprising poly dT, the cell of origin barcodes for the bead, and optionally a UMI.

In certain embodiments, the protein labeling oligonucleotides are cleavable. In certain embodiments, the mRNA capture oligonucleotides are cleavable. In certain embodiments, the oligonucleotides are chemically-cleavable, enzymatically cleavable, or photocleavable.

In another aspect, the present invention provides for a method of measuring proteins in single cells comprising: segregating single cells into discrete volumes; covalently labeling proteins from the single cells with protein labeling oligonucleotides, said oligonucleotides comprising cell of origin barcodes; optionally, pooling the discrete volumes; labeling the proteins with one or more affinity ligands each specific for a target protein, wherein the one or more affinity ligands are linked to an ABC oligonucleotide comprising an antibody barcode (ABC) specific for the target protein, wherein each ABC oligonucleotide is configured for hybridizing to the protein labeling oligonucleotides and extending the cell of origin barcodes; incubating the sample with extension reagents under isothermal conditions; and sequencing the extended ABC oligonucleotides present in the sample, thereby identifying proteins in single cells. The method may further comprise capturing mRNA on capture oligonucleotides comprising poly dT, the cell of origin barcodes for the discrete volume, and optionally a UMI.

In certain embodiments, the discrete volumes comprise droplets, microfluidic chambers, or microwells. The discrete volumes may be droplets comprising beads labeled with the protein labeling oligonucleotides. The protein labeling oligonucleotides may be cleavable. The beads may be further labeled with the mRNA capture oligonucleotides. The mRNA capture oligonucleotides may be cleavable.

In another aspect, the present invention provides for an oligonucleotide-labeled bead for analyzing proteins expressed in single cells, wherein said bead comprises a plurality of first oligonucleotides, wherein each of said first oligonucleotides comprises: a cleavable linker directly attached to the bead; a protein linking moiety; a cell barcode sequence, wherein the cell barcode sequence is the same across all oligonucleotides on said bead, but varies among the oligonucleotides on any other individual bead; and a universal hybridization sequence. The linker may be chemically-cleavable, enzymatically cleavable, or photocleavable. The protein linking moiety may be a photoreactive group configured to covalently link to proteins upon experimentally defined illumination. The protein linking moiety may be a click chemistry group configured to covalently link to proteins.

In certain embodiments, the oligonucleotide-labeled bead may further comprise a plurality of second oligonucleotides on said bead, said second oligonucleotides comprising: a linker directly attached to the bead; the cell barcode sequence; and an oligonucleotide redundant sequence for capturing polyadenylated mRNAs and priming reverse transcription. The oligonucleotide sequence for capturing polyadenylated mRNAs and priming reverse transcription may be an oligo dT sequence. Each second oligonucleotide may comprise a Unique Molecular Identifier (UMI). The second oligonucleotide linker may be chemically-cleavable, enzymatically cleavable, or photocleavable.

In certain embodiments, the second oligonucleotide linker is differentially cleavable as compared to the first oligonucleotide linker, whereby each linker is capable of cleavage at experimentally defined times.

In certain embodiments, the second oligonucleotides comprise 1-5% of oligonucleotides on said bead and the oligonucleotides for protein linking comprise 95-99% of oligonucleotides on said bead.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1B shows simultaneously with (A), DNA antibody barcodes copy nearby antenna identity. FIG. 1C shows a schematic of DNA antenna labeling of membrane proteins, cyclic production of reporter DNA, and in silico antenna graph reconstruction. (top) and antibody-antenna recording to map abundance, co-localization and spatial patterns at nanometer scale. (bottom)

FIG. 2B shows pairwise proximity ligation to enable intracellular protein abundance readout. FIG. 2C shows building a complex specific DNA antenna network to enable quantification of complex compositions and protein-protein interactions. FIG. 2D shows tagmentation of genomic DNA with custom adaptors to enable readout of protein complex-DNA interactions.

Figures 1A, 1B:
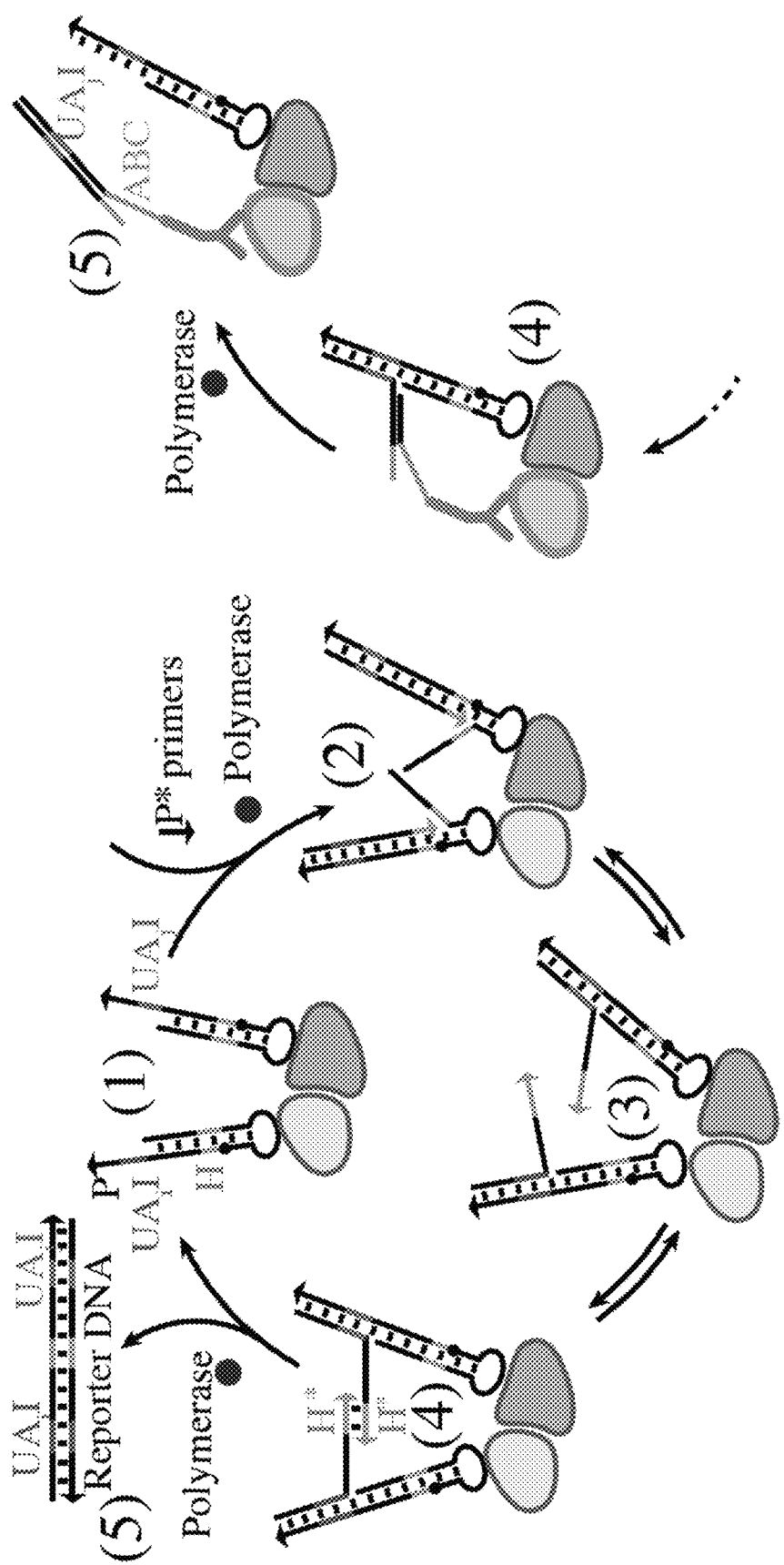
FIG. 1A-FIG. 1C—FIG. 1A shows cyclic, isothermal process of antenna proximity recording which produces reporter DNA coding for the identities (UAIs) of proximal antennas. H is a short palindrome.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to International Patent numbers PCT/US16/059233, filed Oct. 27, 2016, PCT/US2016/059195, filed Oct. 27, 2016, and PCT/US16/059230 filed Oct. 27, 2016.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide for novel methods and systems for quantifying protein abundances, protein modifications and protein interactions. In further embodiments, the present invention provides for novel methods and systems for determining spatial patterning of proteins and protein modifications over the genome of a cell. The systems and methods disclosed herein can also be applied to single cells.

It is an objective of the present invention to determine protein expression using a sequencing readout. It is another objective of the present invention to determine protein expression and gene expression in single cells. It is another object of the present invention to detect protein-protein and/or protein-RNA proximity in bulk cells or in a single cell using a sequencing readout. It is another objective of the present invention to map proteins and protein modifications to genomic loci.

Prior studies have used auto-cycling reporters linked to antibodies to determine proteins that are within a specific proximity to each other as defined by the reporters (Schaus et al., A DNA nanoscope via auto-cycling proximity recording, Nature Communications 8:696). The prior methods do not allow specific protein complexes to be identified. For example, one protein A may be in proximity with Protein B in one complex and another Protein A may be in proximity with Protein C in another complex. Using the auto-cycling reporters linked to antibodies, one may incorrectly suggest that protein A, B, and C are in a single protein complex. Here, applicants determine relative spatial positioning of biomolecules in reference to an antenna network. The antenna network is established on biomolecules using a novel library of auto-cycling reporters (antennas). Each antenna has a unique identifier sequence (AUI) such that the precise spatial location of each antenna in the network can be identified. Using oligonucleotide-labeled affinity ligands (e.g., antibodies) and optionally, tagmentation adaptor molecules both capable of recording the unique identifier sequence allows for determining exact spatial proximity relative to the antenna network. The reporter molecules generated by antenna molecules, antibody oligonucleotides and/or adaptor molecules are read using high-throughput sequencing, followed by image production by computational reconstruction of the antenna network and molecular targets. Thus, spatial location of a plurality of proteins and genomic locations can be determined and not merely proteins in specified proximity to each other.

Embodiments disclosed herein provide methods and apparatuses for single-cell proteomic analysis. In certain embodiments, the methods leverage the use of protein specific affinity ligands (e.g., antibodies), microfluidics, and barcoding to provide a sequencing based readout for quantifying protein expression and protein-protein proximity in single cells. Additional embodiments provide for coupling proteomic and gene expression analysis in single cells. Additional embodiments also provide for detecting protein proximity to genomic loci in single cells.

Establishing Antenna Network

In certain embodiments, an antenna network is established over a biological sample comprising discrete biological modules.

As used herein, "biological modules" refers to any separate compartment or biological unit. A biological module may include a plurality of biomolecules (e.g., proteins, nucleic acids). A biological module may be a single protein complex in solution. The biological module may be a complex of protein and nucleic acid. For example, a biological module may be a single mononucleosome comprising modified histones and genomic DNA. The biological module may be an RNA binding protein complex bound to RNA. A biological module may also include an entire cell or a small population of interacting cells. A biological module may also include any membrane bound structure, such as an organelle or exosome.

As used herein, a "biomolecule" is any molecule that is produced by a living organism, including large macromolecules such as proteins, polysaccharides, lipids and nucleic acids (e.g., DNA and RNA such as mRNA), as well as small molecules such as primary metabolites, secondary metabolites, and natural products. In certain embodiments, a biomolecule is a protein target such as, for example, proteins of a cellular environment (e.g., intracellular or membrane proteins). In certain embodiments, a biomolecule is a protein modification such as, for example, a histone modification or a modification on a membrane protein.

Auto-cycling reporter molecules have been described (see, e.g., US20180010174A1). Applicants apply the concept of auto-cycling reporters to generate, for the first time, an antenna network. As used herein, "antenna network" refers to a self-reporting network of antenna molecules conjugated to discrete biological modules. As used herein, "Unique Antenna Identifier" or "UAI" refers to refers to a unique molecular identifier sequence specific for each antenna molecule. The antenna network self-reports the location of antenna molecules in proximity at set distances. The antenna molecules can generate a reporter molecule indicating the relative location of the antenna to other antenna molecules in the network. A map of the antenna network can then be formed by sequencing of the reporter molecules.

Biomolecules within biological modules can be mapped to the antenna network based on their proximity to an antenna molecule. Two antenna molecules or an antenna molecule and a biomolecule are considered to be "proximate" to each other if the distance between the two molecules is 0 nM to 100 nM. For example, the distance between two molecules proximate to each other may be 0 nM to 5 nM, 0 nM to 10 nM, 0 nM to 20 nM, 0 nM to 30 nM, 0 nM to 40 nM, or 0 nM to 50 nM. In preferred embodiments, the distance between two molecules proximate to each other may be 6 to 40 nM. Biomolecules can be mapped to the antenna network by labeling the biomolecules with oligonucleotides configured to capture the UAI. For example, oligonucleotide linked antibodies can be used to label proteins or protein modifications or genomic DNA may be labeled by tagmentation with adaptor oligonucleotides. The oligonucleotides may be configured to hybridize with the antenna molecules in proximity and capture the UAI sequence.

The UAI from an antenna that is in proximity to an antibody or adaptor molecule can be transferred to the antibody linked oligonucleotide or adaptor molecule in an irreversible reaction. The antenna molecule can be regenerated by primer binding and extension, such that a UAI can be transferred to another antibody linked oligonucleotide or adaptor molecule, or another antenna network reporter molecule can be generated.

Since biological modules in a sample will rarely interact with other biological modules, reporter molecules generated by biological modules in proximity will be far less than reporter molecules generated by biomolecules that are part of a biological module (e.g., a cell or protein complex). Therefore, antenna molecules can be mapped to specific biological modules. Once a reporter molecule comprising unique antenna sequences is generated, the antenna is regenerated by extension of primers specific for the antenna network. The antenna network also provides for the transfer of UAI sequences to other reporter molecules in proximity. In certain embodiments, proteins are labeled with affinity ligands (e.g., antibodies, aptamers) linked to oligonucleotides. The oligonucleotides are capable of transferring a UAI to itself establishing the location of the protein in the antenna network and thus to individual biological modules. Labeling the biological modules with many affinity ligands can then allow spatial location of many proteins in the antenna network. The proteins or nucleic acids may not necessarily be in direct proximity to each other, but based on the antenna network location, protein complexes, including multiple proteins, can be identified.

In certain embodiments, the antenna molecules comprise one or more nucleic acid strands arranged into a double-stranded palindromic region, a hybridization region, a double-stranded UAI region, and a primer-binding region. In certain embodiments, the antenna molecules are arranged to form a hairpin structure, which is a single stretch of contiguous nucleotides that folds and forms a double-stranded region, referred to as a "stem," and a single-stranded region, referred to as a "loop." The double-stranded region is formed when nucleotides of two regions of the same nucleic acid base pair with each other. In certain embodiments, the "UAI oligonucleotide" refers to the oligonucleotide sequence comprising the primer extended through the UAI, hybridization sequence and palindromic sequence. Thus the UAI oligonucleotide sequence may comprise from 5' to 3' the primer sequence, UAI sequence, hybridization sequence and palindromic sequence.

In certain embodiments, the antenna molecules comprise two parallel nucleic acid strands (e.g., as two separate nucleic acids or as a contiguous folded hairpin). One of the strands is referred to as a "complementary strand," and the other strand is referred to as a "displacement strand." The complementary strand typically contains the primer-binding region, or at least a single-stranded segment of the primer-binding region, where the primer binds (e.g., hybridizes). The complementary strand and the displacement strand are bound to each other at least through a double-stranded UAI region and through a double-stranded palindromic region. The "displacement strand" is the strand that is initially displaced by a newly-generated UAI oligonucleotide, as described herein, and, in turn, displaces the newly-generated UAI oligonucleotide as the displacement strand "re-binds" to the complementary strand. Thus, the UAI oligonucleotide is displaced and generates a free 3' end comprising the palindromic sequence followed by a hybridization sequence and UAI sequence.

The antenna molecules can be synthesized as single oligonucleotides or as two parallel strands using standard oligonucleotide synthesis techniques.

Two nucleic acids or two nucleic acid regions are "complementary" to one another if they base-pair, or bind, to each other to form a double-stranded nucleic acid molecule via Watson-Crick interactions (also referred to as hybridization). As used herein, "binding" refers to an association between at least two molecules due to, for example, electrostatic, hydrophobic, ionic and/or hydrogen-bond interactions under physiological conditions.

A "double-stranded region" of a nucleic acid refers to a region of a nucleic acid (e.g., DNA or RNA) containing two parallel nucleic acid strands bound to each other by hydrogen bonds between complementary purines (e.g., adenine and guanine) and pyrimidines (e.g., thymine, cytosine and uracil), thereby forming a double helix. In certain embodiments, the two parallel nucleic acid strands forming the double-stranded region are part of a contiguous nucleic acid strand. For example, as discussed above, the present disclosure provides antenna molecules in the form of hairpin structures.

A "single-stranded region" of a nucleic acid refers to a region of a nucleic acid containing a single nucleic acid strand, unbound to (unpaired with) a second nucleic acid strand. It should be understood that a antenna molecule in the form of a hairpin structure contains both a double-stranded region (a paired region), referred to as the "stem," and a single-stranded region (an unpaired region), referred to as the "loop," as discussed above.

A "double-stranded palindromic region" refers to a region of a nucleic acid (e.g., DNA or RNA) barcoded probe that is the same sequence of nucleotides whether read 5' (five-prime) to 3' (three prime) on one strand or 5' to 3' on the complementary strand with which it forms a double helix. For example, the following sequence, is considered a palindromic sequence: ACCGGT. Thus, a double-stranded palindromic region containing the foregoing sequence is arranged, as follows:

5'-ACCGGT-3'
3'-TGGCCA-5';

Palindromic sequences permit joining of antenna molecules that are proximate to each other. In certain embodiments the palindromic sequence is followed in the 5' direction by a hybridization sequence followed by the UAI sequence. Thus, an oligonucleotide linked to a biomolecule can hybridize to the hybridization sequence and extend the UAI sequence. Polymerase extension of a primer bound to the primer-binding region produces the UAI oligonucleotide which refers to the newly generated nucleic acid strand. Generation of the UAI oligonucleotide displaces one of the strands of the antenna molecule, referred to as the "displacement strand." This displacement strand, in turn, displaces a portion of the UAI oligonucleotide (by binding to its "complementary strand"), starting at the 3' end, enabling the 3' end of the UAI oligonucleotide, containing the palindromic sequence, to bind to another UAI oligonucleotide similarly displaced from a proximate antenna molecule or to bind to an oligonucleotide linked to a biomolecule. Typically, but not always, the reaction takes place at 37° C. in the presence of a displacing polymerase. As used herein "strand displacement" refers to the mechanism by which two nucleic acid strands with identical sequences, when proximate to a single complementary nuclei acid strand (or segment of a strand), undergo relatively rapid (e.g., timescale <1 s) competition for that complement strand, 'displacing' each other from the complement presumably by a 'random-walk' mechanism.

In certain embodiments, a double-stranded palindromic region has a length of 4 to 10 nucleotide base pairs. That is, in certain embodiments, a double-stranded palindromic region may comprise 4 to 10 contiguous nucleotides bound to 4 to 10 respectively complementary nucleotides. For example, a double-stranded palindromic region may have a length of 4, 5, 6, 7, 8, 9 or 10 nucleotide base pairs. In certain embodiments, a double-stranded palindromic region may have a length of 5 to 6 nucleotide base pairs. In certain embodiments, the double-stranded palindromic region is longer than 10 nucleotide base pairs. For example, the double-stranded palindromic region may have a length of 4 to 50 nucleotide base pairs. In certain embodiments, the double-stranded palindromic region has a length of 4 to 40, 4 to 30, or 4 to 20 nucleotide base pairs.

A double-stranded palindromic region may comprise guanine (G), cytosine (C), adenine (A) and/or thymine (T). In certain embodiments, the percentage of G and C nucleotide base pairs (G/C) relative to A and T nucleotide base pairs (A/T) is greater than 50%. For example, the percentage of G/C relative to A/T of a double-stranded palindromic region may be 50% to 100%. In certain embodiments, the percentage of G/C relative to A/T is greater than 60%, 65%, 70%, 75%, 80%, 85%, 90%, 95%.

In certain embodiments, a double-stranded palindromic region may include an even number of nucleotide base pairs, although double-stranded palindromic region of the present disclosure are not so limited. For example, a double-stranded palindromic region may include 4, 6, 8 or 10 nucleotide base pairs. Alternatively, a double-stranded palindromic region may include 5, 7 or 9 nucleotide base pairs.

A "double-stranded sequence comprising a unique antenna identifier (UAI) sequence" refers to a double-stranded region of a nucleic acid (e.g., DNA or RNA) antenna molecule that identifies the antenna molecule. A double-stranded sequence comprising a unique antenna identifier (UAI) sequence may comprise any combination of nucleotides in random or rationally-designed order. In certain embodiments, a UAI region has a length of 2 to 100 nucleotide base pairs. That is, in certain embodiments, a UAI region may comprise 2 to 100 contiguous nucleotides bound to 2 to 100 respectively complementary nucleotides. For example, a UAI region may have a length of 2, 3, 4, 5, 6, 7, 8, 9, 10, 11, 12, 13, 14, 15, 16, 17, 18, 19 or 20 nucleotide base pairs. In certain embodiments, a UAI region may have a length of 2 to 5, 2 to 10, 2 to 15, 2 to 20, 2 to 25, 2 to 30, 2 to 35, 2 to 40, 2 to 45, or 2 to 50 nucleotide base pairs. In certain embodiments, a UAI region may have a length of 35 to 50, 35 to 60, 35 to 70, 35 to 80, 35 to 90, or 35 to 100 nucleotide base pairs. In certain embodiments, a UAI region is longer than 100 nucleotide base pairs. For example, a UAI region may have a length of 2 to 200 nucleotide base pairs. In certain embodiments, a UAI region has a length of 2 to 190, 2 to 180, 2 to 170, 2 to 160, 2 to 150, 2 to 140, 2 to 130, 2 to 120, or 2 to 110 nucleotide base pairs.

A "primer-binding region" refers to a region of a nucleic acid (e.g., DNA or RNA) antenna molecule where a single-stranded primer (e.g., DNA or RNA primer) binds to start replication. A primer-binding region may be a single-stranded region or a partially double-stranded region, which refers to a region containing both a single-stranded segment and a double-stranded segment. A primer-binding region may comprise any combination of nucleotides in random or rationally-designed order. In certain embodiments, a primer-binding region has a length of 4 to 40 nucleotides (or nucleotide base pairs, or a combination of nucleotides and nucleotide base pairs, depending on the single- and/or double-stranded nature of the primer-binding region). For example, a primer-binding region may have a length of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides (and/or nucleotide base pairs). In certain embodiments, a primer-binding region may have a length of 4 to 10, 4 to 15, 4 to 20, 4 to 25, 4 to 30, 4 to 35, or 4 to 40 nucleotides (and/or nucleotide base pairs). In certain embodiments, a primer-binding region is longer than 40 nucleotides. For example, a primer-binding region may have a length of 4 to 100 nucleotides. In certain embodiments, a primer-binding region has a length of 4 to 90, 4 to 80, 4 to 70, 4 to 60, or 4 to 50 nucleotides.

In certain embodiments, a primer-binding region is designed to accommodate binding of more than one (e.g., 2 or 3 different) primers.

A "primer" is a single-stranded nucleic acid that serves as a starting point for nucleic acid synthesis. A polymerase adds nucleotides to a primer to generate a new nucleic acid strand. Primers of the present disclosure are designed to be complementary to and to bind to the primer-binding region of an antenna molecule. Thus, primer length and composition (e.g., nucleotide composition) depend, at least in part, on the length and composition of a primer-binding region of an antenna molecule. In certain embodiments, a primer has a length of 4 to 40 nucleotides. For example, a primer may have a length of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. In certain embodiments, a primer may have a length of 4 to 10, 4 to 15, 4 to 20, 4 to 25, 4 to 30, 4 to 35, or 4 to 40 nucleotides.

In certain embodiments, a primer comprises at least one nucleotide mismatch relative to the single-stranded primer-binding region. Such a mismatch may be used facilitate displacement of a UAI oligonucleotide from the complementary strand of an antenna molecule. In certain embodiments, a primer comprises at least one artificial linker.

In certain embodiments, extension of a primer (bound to a primer-binding site) by a displacing polymerase is typically terminated by the presence of a molecule or modification that terminates polymerization. Thus, in certain embodiments, antenna molecules of the present disclosure comprise a molecule or modification that terminates polymerization. A molecule or modification that terminates polymerization ("stopper" or "blocker") is typically located in a double-stranded region of a barcoded probe, adjacent to the double-stranded palindromic region, such that polymerization terminates extension of the primer through the double-stranded palindromic region. For antenna molecules arranged in the form of a hairpin, a molecule or modification that terminates polymerization may be located between the double-stranded palindromic region and the hairpin loop. In certain embodiments, the molecule that terminates polymerization is a synthetic non-DNA linker, for example, a triethylene glycol spacer, such as the Int Spacer 9 (iSp9) or Spacer 18 (Integrated DNA Technologies (IDT)). It should be understood that any non-native linker that terminates polymerization by a polymerase may be used as provided herein. Other non-limiting examples of such molecules and modifications include a three-carbon linkage (/iSpC3/) (IDT), ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

A "strand-displacing polymerase" refers to a polymerase that is capable of displacing downstream nucleic acid (e.g., DNA) encountered during nucleic acid synthesis. Different polymerases can have varying degrees of displacement activity. Examples of strand-displacing polymerases include, without limitation, Bst large fragment polymerase (e.g., New England Biolabs (NEB) #M0275), phi 29 polymerase (e.g., NEB #M0269), Deep VentR polymerase, Klenow fragment polymerase, and modified Taq polymerase. Other strand-displacing polymerases are contemplated.

In certain embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with Iso-dG but not with dG. Similarly, Iso-dG will base pair with Iso-dC but not with dC. By incorporating these nucleotides in a pair on opposite sides of the hairpin, at the stopper position, the polymerase will be halted, as it does not have a complementary nucleotide in solution to add at that position.

In certain embodiments, the efficiency of performance of a "stopper" or "blocker" modification can be improved by lowering dNTP concentrations (e.g., from 200 µM) in a reaction to 100 µM, 10 µM, 1 µM, or less.

Inclusion of a molecule or modification that terminates polymerization often creates a "bulge" in a double-stranded region of a barcoded probe (e.g., a stem region for hairpin structures) because the molecule or modification is not paired. Thus, in certain embodiments, antenna molecules are designed to include, opposite the molecule or modification, a single nucleotide (e.g., thymine), at least two of same nucleotide (e.g., a thymine dimer (TT) or trimer (TTT)), or an non-natural modification.

Thus, to prevent the polymerase from extending an end (e.g., a 5' or 3' end) of an antenna molecule, a poly-T sequence (e.g., a sequence of 2, 3, 4, 5, 7, 8, 9 or 10 thymine nucleotides) may be used. Alternatively, a synthetic base (e.g., an inverted dT) or other modification may be added to an end (e.g., a 5' or 3' end) of an antenna molecule to prevent unwanted polymerization of the antenna. Other termination molecules (molecules that prevent extension of a 3' end not intended to be extended) include, without limitation, iso-dG and iso-dC or other unnatural nucleotides or modifications.

As discussed herein, generation of a UAI oligonucleotide displaces one of the strands of the antenna molecule. This displaced strand, in turn, displaces a portion of the UAI oligonucleotide, starting at the 3' end. This displacement of the UAI oligonucleotide is facilitated, in certain embodiments, by a "double-stranded displacement region" adjacent to the molecule or modification that terminates polymerization. In embodiments wherein the antenna molecule has a hairpin structure, the double-stranded displacement region may be located between the molecule or modification that terminates polymerization and the hairpin loop. A double-stranded displacement region may comprise any combination of nucleotides in random or rationally-designed order. In certain embodiments, a double-stranded displacement region has a length of 2 to 10 nucleotide base pairs. For example, a double-stranded displacement region may have a length of 2, 3, 4, 5, 6, 7, 8, 9 or 10 nucleotide base pairs. In certain embodiments, a double-stranded palindromic region may have a length of 5 to 6 nucleotide base pairs. In certain embodiments, a double-stranded palindromic region may contain only a combination of C and G nucleotides.

Displacement of the UAI oligonucleotide may also be facilitated, in certain embodiments, by modifying the reaction conditions. For example, some auto-cyclic reactions may include, instead of natural, soluble dNTPs for new strand generation, phosphorothioate nucleotides (2'-Deoxynucleoside Alpha-Thiol 2'-Deoxynucleoside Alpha-Thiol Triphosphate Set, Trilink Biotechnologies). These are less stable in hybridization than natural dNTPs, and result in a weakened interaction between UAI oligonucleotide and stem. They may be used in any combination (e.g., phosphorothioate A with natural T, C, and G bases, or other combinations or ratios of mixtures). Other such chemical modifications may be made to weaken the UAI oligonucleotide pairing and facilitate displacement.

Similarly, the antenna molecule itself may be modified, in certain embodiments, with unnatural nucleotides that serve instead to strengthen the hairpin stem. In such embodiments, the displacing polymerase that generates the UAI oligonucleotide can still open and copy the stem, but, during strand displacement, stem sequence re-hybridization is energetically favorable over UAI oligonucleotide hybridization with stem template. Non-limiting examples of unnatural nucleotides include 5-methyl dC (5-methyl deoxycytidine; when substituted for dC, this molecule increase the melting temperature of nucleic acid by as much as 5° C. per nucleotide insertion), 2,6-diaminopurine (this molecule can increase the melting temperature by as much as 1-2° C. per insertion), Super T (5-hydroxybutynl-2'-deoxyuridine also increases melting temperature of nucleic acid), and/or locked nucleic acids (LNAs). They may occur in either or both strands of the hairpin stem.

In certain embodiments, unnatural nucleotides may be used to introduce mismatches between new UAI oligonucleotide sequence and the stem. For example, if an isoG nucleotide existed in the template strand of the stem, a polymerase, in some cases, will mistakenly add one of the soluble nucleotides available to extend the UAI oligonucleotide, and in doing so create a 'bulge' between the new UAI oligonucleotide and the stem template strand, much like the bulge (included in the primer). It will serve the same purpose of weakening UAI oligonucleotide-template interaction and encourage displacement.

In certain embodiments, antenna molecules of the present disclosure are arranged to form a hairpin structure, which is a single stretch of contiguous nucleotides that folds and forms a double-stranded region, referred to as a "stem," and a single-stranded region, referred to as a "loop." In certain embodiments, the single-stranded loop region has a length of 3 to 50 nucleotides. For example, the single-stranded loop region may have a length of 3, 4, 5, 6, 7, 8, 9 or 10 nucleotides. In certain embodiments, the single-stranded loop region has a length of 3 to 10, 3 to 15, 3 to 20, 3 to 25, 3 to 30, 3 to 35, 3 to 40, 3 to 45, or 3 to 50 nucleotides. In certain embodiments, the single-stranded loop region is longer than 50 nucleotides. For example, the single-stranded loop region may have a length of 3 to 200 nucleotides. In certain embodiments, the single-stranded loop region has a length of 3 to 175, 3 to 150, 3 to 100, or 3 to 75 nucleotides. In certain embodiments, a loop region includes smaller regions of intramolecular base pairing. A hairpin loop, in certain embodiments permits flexibility in the orientation of the antenna molecule relative to a target binding-moiety. That is, the loop typically allows the antenna molecule to occupy a variety of positions and angles with respect to the binding moiety, thereby permitting interactions with a multitude of nearby antenna molecules, ABC oligonucleotides or adapter oligonucleotides.

Antenna molecules of the present disclosure are typically attached to proteins in or on the discrete biological modules through a binding moiety. In certain embodiments, the binding moiety is attached to an end of the antenna molecule (e.g., the end distal to the primer-binding region). In certain embodiments, the binding moiety is attached to the single-stranded loop region of an antenna molecule arranged in the form of a hairpin. The antenna molecules can be conjugated to the discrete biological modules by any method known in the art (e.g., without limitation, biotin, aptamers, nanobodies, nucleic acids, a drug and atoms (e.g., Li)). In certain embodiments, the antenna molecules are covalently conjugated.

In certain embodiments, cells can be non-specifically labeled with antenna molecules. For instance, primary amines or thiols of extracellular domains of membrane proteins can be labeled with click chemistry moieties (see, e.g., Niki'c et al., Labeling proteins on live mammalian cells using click chemistry. Nature protocols, 10(5):780-791, 2015; Chang, et al., Copper-free click chemistry in living animals. PNAS 2010 107 (5) 1821-1826; published ahead of print Jan. 14, 2010; Hong et al., Labeling Live Cells by Copper-Catalyzed Alkyne-Azide Click Chemistry. Bioconjug Chem. 2010 Oct. 20; 21(10): 1912-1916; Kolb, H. C., Finn, M. G. and Sharpless, K. B. (2001), Click Chemistry: Diverse Chemical Function from a Few Good Reactions. Angewandte Chemie International Edition, 40: 2004-2021; and Hoyle, Charles E. and Bowman, Christopher N. (2010), Thiol-Ene Click Chemistry. Angewandte Chemie International Edition, 49: 1540-1573), and in a staining step, oligonucleotides functionalized with compatible click chemistry groups can be covalently attached. In certain embodiments, copper-less click chemistry reagents may be used to label the proteins (e.g., Click-iT® DIBO-maleimide can be used to label thiols and Click-iT® DIBO-succinimidyl ester can be used to label primary amines).

In additional embodiments, one could biotinylate primary amines of proteins, and stain samples with monomeric avidin and biotin linked antenna molecules or with avidin labeled antenna molecules (see, e.g., Jeong Min Lee, et al., A rhizavidin monomer with nearly multimeric avidin-like binding stability against biotin conjugates. Angewandte Chemie International Edition, 55(10):3393-3397, 2016), or antibodies that recognize biotin (see, e.g., Udeshi, et al., Antibodies to biotin enable large-scale detection of biotinylation sites on proteins. Nature Methods, 2017) that are conjugated to DNA sample barcodes. This reaction would be non-specific, and efficient.

In certain embodiments, the surface of the cells is labeled with a biotin ester. Biotin-XX sulfosuccinimidyl ester is a cell-impermeant, amine-reactive compound that can be used to label proteins exposed on the surface of live cells (see, e.g., Cell-Surface Biotinylation Kit, ThermoFisher Scientific). The sulfosuccinimidyl ester forms an extremely stable conjugate (Bioconjugate Chem 6, 447 (1995)) with cell-surface proteins, and the biotin provides a convenient hapten for subsequent analysis or binding with an avidin-based protein (e.g., linked to an antenna oligonucleotide), including streptavidin, NeutrAvidin or CaptAvidin biotin-binding proteins (Cell Biology: A Laboratory Handbook 2nd Edition, J. Celis, Ed., pp. 341-350, Academic Press (1998)) Cell-surface biotinylation techniques have been employed to differentially label proteins in the apical and basolateral plasma membranes of epithelial cells (J Neurochem 77, 1301 (2001); J Cell Sci 109, 3025 (1996)). The technique is also suited to the study of internalization of membrane proteins and cell-surface targeting of proteins (J Cell Biol 153, 957 (2001); J Virol 75, 4744 (2001); J Biol Chem 274, 36801 (1999)).

The "cycling rate" of an antenna molecule, as provided herein, refers to the rate at which a UAI reporter molecule is produced, resulting from the cyclic interaction of two proximate antenna molecules or an antenna molecule and biomolecule. In certain embodiments, a primer comprising a mismatch or an artificial linker increases the cycling rate by 5-fold to 10-fold, or more.

"Extension conditions that permit production of reporter molecules" may be physiological conditions (e.g., a temperature of 20-40 degrees Celsius, atmospheric pressure of 1, and/or a pH value of 6-8). In certain embodiments, extension is performed at a temperature of 20 to 40 degrees Celsius (° C.). For example, extension may be performed at a temperature of 20° C., 21° C., 22° C., 23° C., 24° C., 25° C., 26° C., 27° C., 28° C., 29° C., 31° C., 32° C., 33° C., 34° C., 35° C., 36° C., 37° C., 38° C., 39° C. or 40° C.

In certain embodiments, extension is performed for a time of 10 minutes (min) to 24 hours, or more. For example, extension may be performed for a time of 10 min to 3 hours (hr), 10 min to 12 hr, 10 min to 18 hr, or 10 min to 24 hr. In certain embodiments, extension is performed for a time of 10 min, 15 min, 20 min, 25 min, 30 min, 35 min, 40 min, 45 min, 50 min, 55 min, 60 min, 65 min, 70 min, 75 min, 80 min, 85 min, 90 min, 95 min, 100 min, 105 min, 110 min, 115 min, 120 min, 125 min, 130 min, 135 min, 140 min, 145 min, 150 min, 155 min, 160 min, 165 min, 170 min, 175 min or 180 min.

In certain embodiments, a salt concentration of 0.25-15 mM Mg and/or 50-250 mM Na is used for extension.

In certain embodiments, reaction dNTPs concentrations for extension may be 0.05-5 mM (e.g., 0.05 mM, 0.10 mM, 0.15 mM, 0.20 mM, 0.25 mM, 0.30 mM, 0.35 mM, 0.40 mM, 0.45 mM, 0.50 mM, 1.0 mM, 1.5 mM, 2.0 mM, 2.5 mM, 3.0 mM, 3.5 mM, 4.0 mM, 4.5 mM or 5.0 mM).

Buffers that may be used include, but are not limited to, "Thermo-Pol Buffer" (New England Biolabs), phosphate buffered saline (with or without Mg or Na supplementation), any commercial or laboratory-prepared cell media, water or any pH-buffered solution supplemented with cationic salts sufficient for DNA hybridization and polymerase operation.

In certain embodiments, the cycling rate as provided herein, is 1 reporter molecule per 10 minutes per pair of molecules in proximity, but may be as rapid as 1 reporter molecule per second or as slow as 1 reporter molecule per 10 hours under certain (e.g., more restrictive) conditions.

From the sequencing data obtained, the spatial arrangement of antenna molecules and biomolecules, relative to one another, can be determined. For example, the sequencing data may be processed computationally to produce a representative antenna network with biomolecules superimposed on top of the network. Such computer code may read sequencing data files, create a digitally-encoded network of associated UAI-UAIs, UAI-ABCs, UAI-adaptors, and UAI-cell barcodes. Any number of commercially available (e.g., Mathematica) or independently-written codes are available for transforming this non-geometric digital representation into one describing relative spatial positioning (known mathematically as aspects of 'graph theory').

Affinity Ligands

An affinity ligand of the present invention may be any oligonucleotide linked molecule capable of specifically binding to a "biomolecule" or a "molecular target." Affinity ligands may be specific for a "biomolecule" or a "molecular target." The "biomolecule" or a "molecular target" may be any molecule that one wishes to observe or quantitate. Examples of molecular targets include, without limitation, proteins, protein modifications, saccharides (e.g., polysaccharides), lipids, nucleic acids (e.g., DNA, RNA, microRNAs), and small molecules. An affinity ligand may be, but is not limited to an antibody, antibody fragment, or aptamer.

An antibody barcode oligonucleotide (ABC) is considered "unique" or "specific" to a molecular target if the barcoded region (ABC) of the oligonucleotide is associated only with that molecular target and can be used to identify only that molecular target among a population of molecules, including other molecular targets identified by their own unique ABC. Similarly, an antibody barcode oligonucleotide (ABC) is considered "unique" or "specific" to a species of molecular target, if the barcoded region of the oligonucleotide is associated only with that molecular target and can be used to identify only that species of molecular target among a population of molecules.

Antibodies

The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, $V_{HH}$ and scFv and/or Fv fragments.

Antibodies may be specific for any target protein or target protein modification. Any protein modification, especially post-translational protein modification, can be assessed by the present method. Exemplary protein modifications that can be assessed by the present method include phosphorylation, acetylation, methylation, ADP-ribosylation, addition of a polypeptide side chain, addition of a hydrophobic group, and addition of a carbohydrate. In one specific embodiment, the phosphorylation to be assessed is phosphorylation on tyrosine, serine, threonine or histidine residue. In another specific embodiment, acetylation to be assessed is acetylation on lysine. In another specific embodiment, methylation to be assessed is methylation on lysine or arginine. In another specific embodiment, the addition of a polypeptide side chain to be assessed is the addition of ubiquitin. In still another specific embodiment, the addition of a hydrophobic group to be assessed is the addition of a fatty acid, e.g., myristate or palmitate, addition of an isoprenoid, e.g., farnesyl or geranylgeranyl, or addition of a glycosyl-phosphatidyl inositol anchor, e.g., a carbohydrate group comprises glycosyl. Probes specific for cholesterol may be used (see, e.g., Gimpl, Cholesterol-Protein Interaction: Methods and Cholesterol Reporter Molecules, Cholesterol Binding and Cholesterol Transport Proteins: Volume 51 of the series Subcellular Biochemistry pp 1-45; and Gimpl and Gehrig-Burger, Probes for studying cholesterol binding and cell biology, Steroids. 2011 February; 76(3):216-31). The present invention may be used with any probe that can be functionalized with an oligonucleotide as described herein.

Methods for attaching nucleic acids to antibodies are well known in the art, and any suitable approach is encompassed within the presently disclosed methods, compositions, and kits (see, e.g., WO2016100976 A2). For example, in some embodiments antibodies may be attached to nucleic acid molecules using the methods described in Gullberg, et al. (2004), PNAS 101(22):8420-8424, and Boozer, et al. (2004), Analytical Chemistry 76(23):6967-6972, both of which are incorporated herein by reference. In some embodiments, antibodies may be attached to nucleic acid molecules by random coupling to free amines. In some embodiments, the antibodies may be attached to nucleic acid molecules by random coupling to free amines using a 10-to-1 ratio of nucleic acid to antibody. In some embodiments, antibodies may be attached to nucleic acid molecules using the methods described in Kozlov, et al. (2004), Biopolymers, 73 621-630, which is incorporated herein by reference. In some embodiments, antibodies may be attached to nucleic acid molecules using hydrazine chemistry. In some embodiments, antibodies may be attached to nucleic acid molecules using "tadpoles" as described in Nolan (2005), Nature Methods 2: 11-12, which is incorporated herein by reference. In general, antibodies may be attached to nucleic acid molecules using any suitable method known in the art for generating engineered antibodies, including the methods described herein. Oligonucleotide linked antibodies are also available commercially (see, e.g., BioLegend, San Diego, CA). In certain embodiments, the hybridization region of an antenna molecule is designed to hybridize with oligonucleotides conjugated to antibodies that are commercially available.

Aptamers

Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double-stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to those described in Rohloff et al., "Nucleic Acid Ligands with Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colorado). In certain embodiments, the present invention may utilize any aptamer specific for a biomolecule and containing any modification as described herein. In certain embodiments, an aptamer is generated having an ABC oligonucleotide as described herein.

Nucleic Acid Barcode, Barcode, and Unique Molecular Identifier (UMI)

The methods provided herein use barcode nucleic acid sequences (e.g., a DNA sequence) to uniquely label each antenna (i.e, UAI), affinity ligands (i.e., ABC oligonucleotide), protein labeling oligonucleotides comprising cell of origin barcodes and cell of origin barcodes. Oligonucleotides linked to affinity ligands specific for a biomolecule comprise the same "barcode." Thus, each affinity ligand comprises a unique barcode sequence (i.e, antibody barcode, ABC).

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with an antenna molecule, a single cell, a labeling ligand (e.g., an antibody), protein, or cDNA such that multiple species can be sequenced together.

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In preferred embodiments, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The target nucleic acid to be sequenced may be a reporter molecule (e.g., UAI-UAI reporter, ABC-UAI reporter, gDNA-adaptor-UAI reporter, or UAI-Cell barcode) as described herein. The UMI may also be used to determine the number of transcripts that gave rise to an amplified product (e.g., when also detecting mRNA levels). In certain embodiments, the amplification is by PCR or multiple displacement amplification (MDA).

In certain embodiments, an UMI with a random sequence of between 4 and 20 base pairs is added to a template, which is amplified and sequenced. In preferred embodiments, the UMI is added to the 5' end of the template. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No: 11, 163-166). Not being bound by a theory, the UMI's are designed such that assignment to the original can take place despite up to 4-7 errors during amplification or sequencing. Not being bound by a theory, an UMI may be used to discriminate between true barcode sequences.

A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Target molecule and/or target nucleic acids can be labeled with multiple nucleic acid barcodes in combinatorial fashion, such as a nucleic acid barcode concatemer. Compositions and methods for concatemerization of multiple barcodes are described, for example, in International Patent Publication No. WO 2014/047561, which is incorporated herein by reference in its entirety.

In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

In some embodiments, the origin-specific barcodes are reversibly coupled to a solid or semisolid substrate. In some embodiments, the origin-specific barcodes further comprise a nucleic acid capture sequence that specifically binds to the target nucleic acids and/or a specific binding agent that specifically binds to the target molecules. In specific embodiments, the origin-specific barcodes include two or more populations of origin-specific barcodes, wherein a first population comprises the nucleic acid capture sequence and a second population comprises the specific binding agent that specifically binds to the target molecules. In some examples, the first population of origin-specific barcodes further comprises a target nucleic acid barcode, wherein the target nucleic acid barcode identifies the population as one that labels nucleic acids. In some examples, the second population of origin-specific barcodes further comprises a target molecule barcode, wherein the target molecule barcode identifies the population as one that labels target molecules.

A nucleic acid barcode may be cleavable from a specific binding agent, for example, after the specific binding agent has bound to a target molecule. In some embodiments, the origin-specific barcode further comprises one or more cleavage sites. In some examples, at least one cleavage site is oriented such that cleavage at that site releases the origin-specific barcode from a substrate, such as a bead, for example a hydrogel bead, to which it is coupled. In some examples, at least one cleavage site is oriented such that the cleavage at the site releases the origin-specific barcode from the target molecule specific binding agent. In some examples, a cleavage site is an enzymatic cleavage site, such as a endonuclease site present in a specific nucleic acid sequence. In other embodiments, a cleavage site is a peptide cleavage site, such that a particular enzyme can cleave the amino acid sequence. In still other embodiments, a cleavage site is a site of chemical cleavage.

Sequencing

In certain embodiments, the nucleic acid of the present invention may be amplified to generate a sequencing library. Any suitable amplification technique may be used, for instance, PCR, assembly PCR, polymerase cycling assembly, reverse transcriptase (RT) PCR amplification, in vitro transcription amplification (IVT), multiple displacement amplification (MDA), or quantitative real-time PCR (qPCR), or the like. The target sequence or template may be amplified within droplets (see, e.g., U.S. Pat. Apl. Pub. No. 2010/0136544, 2014/0199730, or 2014/0199731), or in bulk solution. Multiple displacement amplification (MDA), is a non-PCR-based isothermal method based on the annealing of random hexamers to denatured DNA, followed by strand-displacement synthesis at constant temperature (Blanco et al. J. Biol. Chem. 1989, 264, 8935-8940). It has been applied to samples with small quantities of genomic DNA, leading to the synthesis of high molecular weight DNA with limited sequence representation bias (Lizardi et al. Nature Genetics 1998, 19, 225-232; Dean et al., Proc. Natl. Acad. Sci. U.S.A 2002, 99, 5261-5266). As DNA is synthesized by strand displacement, a gradually increasing number of priming events occur, forming a network of hyper-branched DNA structures. The reaction can be catalyzed by enzymes such as the Phi29 DNA polymerase or the large fragment of the Bst DNA polymerase. The Phi29 DNA polymerase possesses a proofreading activity resulting in error rates 100 times lower than Taq polymerase (Lasken et al. Trends Biotech. 2003, 21, 531-535).

The oligonucleotides according to the present invention may also contain a variety of sequences. For example, the oligonucleotide may contain one or more primer sequences, one or more unique or "barcode" sequences as discussed herein, one or more promoter sequences, one or more spacer sequences, or the like. The oligonucleotide may also contain, in some embodiments one or more cleavable spacers, e.g., photocleavable linker. The oligonucleotide may in some embodiments be attached to a particle chemically (e.g., via a linker) or physically (e.g., without necessarily requiring a linker), e.g., such that the oligonucleotides can be removed from the particle via cleavage. Other examples include portions that may be used to increase the bulk (or length) of the oligonucleotides (e.g., using specific sequences or non-sense sequences), to facilitate handling (for example, an oligonucleotide may include a poly-A tail), to increase selectivity of binding (e.g., as discussed below), to facilitate recognition by an enzyme (e.g., a suitable ligase), to facilitate identification, or the like.

In certain embodiments, the invention involves targeted nucleic acid profiling (e.g., sequencing, quantitative reverse transcription polymerase chain reaction, and the like) (see e.g., Geiss G K, et al., Direct multiplexed measurement of gene expression with color-coded probe pairs. Nat Biotechnol. 2008 March; 26(3):317-25). In certain embodiments, a target nucleic acid molecule (e.g., RNA molecule), may be sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. Methods for constructing sequencing libraries are known in the art (see, e.g., Head et al., Library construction for next-generation sequencing: Overviews and challenges. Biotechniques. 2014; 56(2): 61-77).

In certain embodiments, highly conserved sequences present a technical limitation on some sequencing platforms that utilize fluorescent detection (i.e., Illumina). This can occur with amplicon-based sequencing such as microbiome studies using 16S rRNA for species identification. In certain embodiments, the oligonucleotides of the present invention include highly conserved sequences. For example, conserved hybridization sequences may be used to generate a barcode comprising two indices, whereby the indices are separated by a conserved hybridization sequence. In this situation, the conserved sequences at the beginning of the read will generate the exact same base with each cycle of sequencing, creating problems for the signal detection hardware and software. This limitation is not an issue with Ion Torrent systems (not fluorescence-based) and can be addressed on Illumina systems by sequencing multiple different amplicons in the same lane whenever possible. An alternative strategy is to use several PCR primers during PCR of a specific amplicon. Each primer has a different number of bases (typically 1-3 random bases) added to the 5' end to offset/stagger the order of sequencing when adapters are ligated to the amplicons. In one embodiment and as described further herein, the first index may include an additional 1 to 3 random bases to stagger the sequencing of the conserved sequence.

In certain embodiments, the invention involves plate based single-cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

The present invention provides for cell-of-origin barcodes (e.g., protein labeling oligonucleotides and mRNA capture oligonucleotides) introduced to discrete volumes (e.g., wells, droplets, microfluidic chambers). In certain embodiments, protein labeling oligonucleotides comprise a protein binding molecule as described herein (e.g., biotin, click chemistry moiety). In certain embodiments, the protein binding molecule is conjugated to the 5' end of the oligonucleotide, such that the 3' end may hybridize to an AUI oligonucleotide and become extended, thus capturing the AUI sequence on the cell of origin barcode sequence.

In certain embodiments, protein labeling oligonucleotides and/or mRNA capture oligonucleotides are introduced by oligonucleotide adorned (e.g. labeled) solid supports (e.g., beads) to distinguish proteins and optionally, mRNA, between single cells. In certain embodiments, in order for single cells to receive a unique cell barcode, a single cell and single solid support of the present invention may be sorted into individual wells of a multi-well plate, microfluidic reaction chambers, such as by using the Fluidigm C1 system, or preferably, single droplets.

In one embodiment, single cells are sorted into separate wells by dilution of the cells and/or physical movement, such as by pipetting. Cells may also be sorted by any cell sorter known in the art, such as, but not limited to FACS. Each well may include a single barcoded bead of the present invention.

In a preferred embodiment, single-cell analysis is performed using microfluidics. Microfluidics involves microscale devices that handle small volumes of fluids. Microfluidic reactions are generally conducted in microdroplets. The ability to conduct reactions in microdroplets depends on being able to merge different sample fluids and different microdroplets. See, e.g., US Patent Publication No. 20120219947, U.S. Pat. No. 9,364,803 and International Patent Publication No. WO 2014085802 A1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to 10' samples to be screened in a single day. Compartmentalization in droplets increases assay sensitivity by increasing the effective concentration of rare species and decreasing the time required to reach detection thresholds. The use of microfluidics technology reduces cycle times, shortens time-to-results, and increases throughput. Furthermore, incorporation of microfluidics technology enhances system integration and automation. Droplet microfluidics combines these powerful features to enable currently inaccessible high-throughput screening applications, including single-cell and single-molecule assays. See, e.g., Guo et al., Lab Chip, 2012, 12, 2146-2155.

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, WO 2001/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Patent Application Publication No. 2014/0256595; and WO 2011/079176. In a preferred embodiment, single-cell analysis is performed in droplets using methods according to WO 2014085802. Each of these patents and publications is herein incorporated by reference in their entireties for all purposes.

In certain embodiments, the invention involves plate based single-cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

Although cells are used in this example as a source of nucleic acid material and proteins, this is by way of example, and in other embodiments, the nucleic acids and proteins may be introduced into the droplets from other sources, or using other techniques (e.g., nuclei, organelles, viruses). In certain embodiments, the invention involves protein detection in single nuclei. In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

Drop-seq methods and apparatus provides a high-throughput single-cell RNA-Seq and/or targeted nucleic acid profiling (for example, sequencing, quantitative reverse transcription polymerase chain reaction, and the like) where the RNAs or targeted nucleic acids from different cells are tagged individually, allowing a single library to be created while retaining the cell identity of each read. The present invention adapts the methods to provide high-throughput single-cell proteomics analysis using the beads of the present invention. The present invention allows for proteomics analysis, as well as concurrent analysis of RNA or targeted nucleic acid profile. In certain embodiments, the analysis of proteins and mRNA requires the formation of droplets with a single bead, lysing of the cell, capture of nucleic acids and labeling proteins with protein labeling oligonucleotides, wherein the mRNA and proteins are labeled with the same cell of origin barcodes. The conditions for lysing the cell is compatible for capture of mRNA and labeling protein.

Microfluidic devices (for example, fabricated in polydimethylsiloxane), generate sub-nanoliter reverse emulsion droplets. These droplets are used to co-encapsulate proteins and/or nucleic acids with a barcoded bead as described herein. Each bead, for example, is uniquely barcoded so that each drop and its contents are distinguishable. The proteins and/or nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

The invention provides a method for preparing uniquely barcoded mRNA capture microbeads, which has a unique cell barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length two or more bases; 2) repeating this process a large number of times, at least two, and optimally more than twelve, such that, in the latter, there are more than 16 million unique cell barcodes on the surface of each bead in the pool (See, www.ncbi.nlm.nih.gov/pmc/articles/PMC206447).

In certain embodiments, the bead comprises a linker, such that the barcode nucleotides are added to the linker. The linkers may be cleavable as described herein. After the barcode is generated on each bead by split and pool cycles the protein labeling oligonucleotides are conjugated to the barcode sequence (e.g., ligation). In certain embodiments, protein labeling oligonucleotides without the barcode sequence (e.g., comprising a protein binding molecule to generate the barcoded protein labeling oligonucleotides) and mRNA capture oligonucleotides are conjugated to the barcode sequence. The ratio of protein labeling oligonucleotides and mRNA capture oligonucleotides can be adjusted to generate beads with the desired proportion of each oligonucleotide.

Generally, the invention provides a method for preparing a large number of beads, particles, microbeads, nanoparticles, or the like with unique nucleic acid cell barcodes comprising performing polynucleotide synthesis on the surface of the beads in a pool-and-split fashion such that in each cycle of synthesis the beads are split into subsets that are subjected to different chemical reactions; and then repeating this split-pool process in two or more cycles, to produce a combinatorically large number of distinct nucleic acid cell barcodes. The present invention further provides performing a polynucleotide synthesis wherein the synthesis may be any type of synthesis known to one of skill in the art for "building" polynucleotide sequences in a step-wise fashion. Examples include, but are not limited to, reverse direction synthesis with phosphoramidite chemistry or forward direction synthesis with phosphoramidite chemistry. Applicants present a complexed bead and a novel process for producing these beads where nucleotides are chemically built onto the bead material in a high-throughput manner followed by enzymatically attaching aptamer oligonucleotides as described herein. Moreover, Applicants generally describe delivering a "packet" of beads which allows one to deliver millions of sequences into separate compartments and then screen all at once.

In certain embodiments, the hydrogel beads, photocleavable spacers, barcoding method, and oligonucleotide release method are as described in Klein et al., 2015 and Zilionis, et al., 2017. Solid supports (e.g., beads) linked to oligonucleotides are prepared, such that each oligonucleotide comprises a cellular barcode shared by all oligonucleotides attached to the individual solid support. In preferred embodiments, the solid support is a bead. Each oligonucleotide preferably includes a UMI to 'uniquely' define each oligonucleotide on the solid support. The oligonucleotides are conjugated to the solid support in a releasable fashion, for instance by a photocleavable linker, an enzymatically cleavable linker, chemically releasable linker. The linker may also include an acrylamide moiety in order to link to the solid support comprising a hydrogel. In addition, the oligonucleotides contain a sequence for hybridization or ligation to a hybridization sequence of the protein labeling oligonucleotides. In one embodiment, the cellular barcode is generated by a split-pool protocol. The split-pool process may include any process described herein, such as, but not limited to the hybridization-extension protocol described in Klein et al. or by using sticky end ligation, thus yielding unique combinatorial cellular barcodes on each solid support. In the case of beads, beads are split into wells comprising different first barcode indices. After adding the first indices, the beads are pooled and split into wells comprising different second indices. The sticky end ligation can include more than one, preferably, more than two indices, each including more than 2 nucleotides and each having sticky ends compatible with ligation to the previous index. The number of indices can determine the number of cycles of split and pool ligation that are required to generate the desired number of unique barcodes.

The oligonucleotide sequences may be linked, e.g., covalently linked, through primer extension, through ligation, or the like. Any of a wide variety of different techniques may be used, and those of ordinary skill in the art will be aware of many such techniques. The exact joining technique used is not necessarily critical, and can vary between embodiments. Non-limiting examples include ligases or other suitable techniques such as those discussed in U.S. Pat. Apl. Ser. No. 61/981,123, incorporated herein by reference.

The oligonucleotide may be of any suitable length or comprise any suitable number of nucleotides. The oligonucleotide may comprise DNA, RNA, and/or other nucleic acids such as PNA, and/or combinations of these and/or other nucleic acids. In some cases, the oligonucleotide is single-stranded, although it may be double-stranded in other cases.

In one embodiment, the solid support comprises a bead linked to a ssDNA sequence oligonucleotide through a linker, an identical sequence for sequencing, a cell barcode sequence, an UMI, and a sequence for hybridization or ligation to the hybridization sequence of a protein labeling oligonucleotide. The sequence for sequencing may include, but is not limited to a T7 promoter or a PCR priming site for library prep. In certain embodiments, the sequence for sequencing includes, but is not limited to the primer region for Illumina paired end library prep.

A solid support linked to oligonucleotides containing a cell barcode may be prepared for single-cell analysis of target proteins according to the following steps. The protein labeling oligonucleotides may be synthesized using known methods in the art, such that the oligonucleotide comprises a protein binding molecule as described herein. In one embodiment, an oligonucleotide sequence linked to the bead is synthesized as a ssDNA polynucleotide sequence. In certain embodiments, the synthesized oligonucleotide has the structure comprising:

5'-/5Acryd/-[cleavable element]-[NXT1]-[barcode1]-[H1]-[barcode2]-[H2]-3'

The 5Acryd is an acrylamide moiety used to link the oligonucleotide to the solid support.

The [Cleavable element] can include, but is not limited to:
1) /iSpPC/Photocleavable linker, that can be released by UV irradiation.
2) /ideoxyU/Enzymatically cleavable linker wherein incorporation of several deoxyUridine, a base that can be removed by the enzyme uracil-N-deglycosylase (UNG), renders the oligo susceptible to strand scission by for, example, Endonuclease VIII.

The T7 RNA polymerase promoter sequence may be included for linear amplification.

NXT1 includes any primer sequence for sequencing library generation. In one embodiment, NXT1 includes, but is not limited to a primer sequence compatible with Illumina paired end sequencing library generation. NXT1 could serve as primers for PCR amplification. Extended primers could be used for incorporation of a sample specific barcode and Illumina flowcell binding if needed.

The cellular barcode sequence is represented by [Barcode 1] and [barcode 2], but can include any combinatorically constructed barcode sequence. The barcode sequence described is generated by adding two indices to the oligonucleotide sequence by hybridization and extension as for Indrop (Klein et al. 2015), to generate unique cellular barcodes.

[Hybridization sequence 1] comprises any desired hybridization sequence. [Hybridization 2] is configured to hybridize to an oligonucleotide configured for labeling proteins as described herein (e.g., it is bound to a protein binding molecule) and/or an oligonucleotide for generating a poly T sequence. In certain embodiments, protein labeling oligonucleotides with the barcode 2 sequence (e.g., comprising a protein binding molecule to generate the barcoded protein labeling oligonucleotides) and mRNA capture oligonucleotides with the same barcode 2 sequence are conjugated to the barcode sequence. The ratio of protein labeling oligonucleotides and mRNA capture oligonucleotides can be adjusted to generate beads with the desired proportion of each oligonucleotide. Each bead, thus comprises the same cell of origin barcode for all oligonucleotides conjugated.

The invention further provides an apparatus for creating a single-cell sequencing library via a microfluidic system, comprising: an oil-surfactant inlet comprising a filter and a carrier fluid channel, wherein said carrier fluid channel further comprises a resistor; an inlet for an analyte comprising a filter and a carrier fluid channel, wherein said carrier fluid channel further comprises a resistor; an inlet for capture microbeads and lysis reagent comprising a filter and a carrier fluid channel, wherein said carrier fluid channel further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops.

In certain embodiments, provided is a mixture comprising a plurality of microbeads adorned (labeled) with combinations of the following elements: bead-specific oligonucleotide cell barcodes created by the described methods; additional oligonucleotide barcode sequences which vary among the oligonucleotides on an individual bead and can therefore be used to differentiate or help identify those individual oligonucleotide molecules (UMI); additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), protein labeling oligonucleotides for labeling proteins, or random sequences (for priming throughout the transcriptome or genome). In an embodiment, the individual oligonucleotide molecules on the surface of any individual microbead contain all three of these elements, and the third element includes a protein labeling oligonucleotides sequence or oligo-dT. The microbeads preferably comprise a primer sequence for downstream sequencing of the barcodes associated with each bead.

In one embodiment, the single cells are poisson loaded into microwells (Fan et al., 2015). The aqueous droplets or microwells may be simultaneously loaded with barcoded beads, each of which has oligonucleotides including; a "cell barcode" that is the same across all the primers on the surface of any one bead, but different from the cell barcodes on all other beads; a Unique Molecular Identifier (UMI), different on each primer, that enables sequence reads derived from the same original DNA tag (amplification and PCR duplicates) to be identified computationally (Kivioja et al., 2012); and a capture sequence to bind the target proteins and/or oligonucleotides (either amplified PCR products or original DNA tags released by proteinase K treatment, or enzymatic/photonic oligo cleavage). Once the beads are loaded, they can be pooled for amplification and library preparation, and sequencing.

The beads according to the present invention can take multiple forms. Drop-seq beads are polystyrene, oligo functionalized beads, but alternative beads are possible, such as soft beads (polymer gel based beads, e.g., see www.10xgenomics.com/technology), that allow for one on one pairing with cells, as to avoid the poisson loading needed in the drop-seq scheme. This reduces the amount of cells one needs, and makes it possible to analyze rare cell types or clinical samples only available in low amounts of cells. Beads or microspheres may refer to a hydrogel particle (polyacrylamide, agarose, etc.), or a colloidal particle (polystyrene, magnetic or polymer particle, etc.) of 1 to 500 micrometer in size, or other dimensions such as those described herein. The microspheres may be porous in some embodiments.

In some embodiments, the oligonucleotides are introduced into the droplets by initially attaching the oligonucleotides to a particle (e.g., a hydrogel or a polymeric particle), then subsequently releasing the oligonucleotides from the particle after the particle has been incorporated into a droplet. See, e.g., U.S. Pat. Apl. Ser. No. 62/072,944, filed Oct. 30, 2014 or PCT Apl. Ser. No. PCT/US2015/026443, filed on Apr. 17, 2015, entitled "Systems and Methods for Barcoding Nucleic Acids," each incorporated herein by reference. For example, in certain embodiments, the oligonucleotides may also contain a cleavable sequence or linker, or otherwise be releasable from the particles. In certain embodiments, the oligonucleotide may contain one or more cleavable linkers, e.g., that can be cleaved upon application of a suitable stimulus. For example, the cleavable sequence may be a photocleavable linker that can be cleaved by applying light or a cleavable linker that can be cleaved by applying a suitable chemical or enzyme.

The particles may be prepared in some cases such that most or all of the particles have a uniquely distinguishable oligonucleotide, relative to other particles having other distinguishable oligonucleotides. If the particles are present within the droplets at a density of 1 particle/droplet (or less), then once the oligonucleotides are released from the particle, then most or all of the droplets will contain one unique oligonucleotide (or no unique oligonucleotide), thus allowing each droplet (and the nucleic acids contained therein) to be uniquely identified.

In some embodiments, the particles may be encapsulated in droplets, such as microfluidic droplets. Those of ordinary skill in the art will be aware of techniques for encapsulating particles within microfluidic droplets; see, for example, U.S. Pat. Nos. 7,708,949, 8,337,778, 8,765,485, or Int. Pat. Apl. Pub. Nos. WO 2004/091763 and WO 2006/096571, each incorporated herein by reference. In some cases, the particles may be encapsulated at a density of less than 1 particle/droplet (and in some cases, much less than 1 particle/droplet) to ensure that most or all of the droplets have only zero or one particle present in them.

In certain embodiments, the solid support may also comprise a protective or passivating layer that can reduce or minimize non-specific attachment of components (e.g., proteins, nucleic acid molecules) to the binding surface during the assay which may lead to loss of signal. Examples of materials that may be utilized in certain embodiments to form passivating layers include, but are not limited to: polymers, such as poly(ethylene glycol), that repel the non-specific binding of proteins; naturally occurring proteins with this property, such as serum albumin and casein; surfactants, e.g. zwitterionic surfactants, such as sulfobetaines; naturally occurring long-chain lipids; and nucleic acids, such as salmon sperm DNA.

In certain embodiments, tagmentation is used to introduce adaptor sequences to genomic DNA in regions of accessible chromatin (e.g., between individual nucleosomes) (see, e.g., US20160208323A1; US20160060691A1; WO2017156336A1; and Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237):910-4. doi: 10.1126/science.aab1601. Epub 2015 May 7). The adaptor molecules are designed to be able to hybridize with AUI oligonucleotides, such that the AUI in proximity is transferred to the adaptor molecule. Thus, sequencing of the oligonucleotide generated allows the identification of the genomic DNA sequence, adaptor sequence and AUI sequence. In certain embodiments, tagmentation is applied to bulk samples or to single cells in discrete volumes.

Compressed Sensing

Mammalian genomes contain approximately 20,000 genes, and mammalian expression profiles are frequently studied as vectors with 20,000 entries corresponding to the abundance of each gene. It is often assumed that studying gene expression profiles requires measuring and analyzing these 20,000 dimensional vectors, but some mathematical results show that it is often possible to study high-dimensional data in low dimensional space without losing much of the pertinent information. In one embodiment of the present invention, less than 20,000 proteins are detected in single cells. Not being bound by a theory, working in low dimensional space offers several advantages with respect to computation, data acquisition and fundamental insights about biological systems.

In one embodiment, protein targets are chosen that are generally part of gene modules or programs, whereby detection of a protein allows for the ability to infer expression of other proteins present in a module or gene program. Samples are directly compared based only on the measurements of these signature genes.

In alternative embodiments, sparse coding or compressed sensing methods can be used to infer large amounts of data with a limited set of target proteins. Not being bound by a theory, the abundance of each of the 20,000 genes can be recovered from random composite measurements. In this regard, reference is made to Cleary et al., "Composite measurements and molecular compressed sensing for highly efficient transcriptomics" posted on Jan. 2, 2017 at biorxiv.org/content/early/2017/01/02/091926, doi.org/10.1101/091926, incorporated herein by reference in its entirety.

The invention is further described in the following examples, which do not limit the scope of the invention described in the claims.

EXAMPLES

Example 1—Resolving Single-Cell Membrane Protein Abundance and Spatial Patterning with Nanometer Scale Resolution Membrane proteins and their molecular interactions control information flow across a cells boundary by sensing the extracellular environment and initiating appropriate intracellular responses. The present invention may be used to measure membrane protein abundances for hundreds of membrane proteins simultaneously, and to determine how they are spatially organized with respect to each other. Applicants approach utilizes concepts based on recent developments: (1) DNA tagging of antibodies, enabling sequencing based quantification of membrane proteins at the single-cell level [1] and (2) DNA nanoscopy, the ability to record with nanoscale precision the spatial proximity of two DNA molecules [4].

Figure 1C:
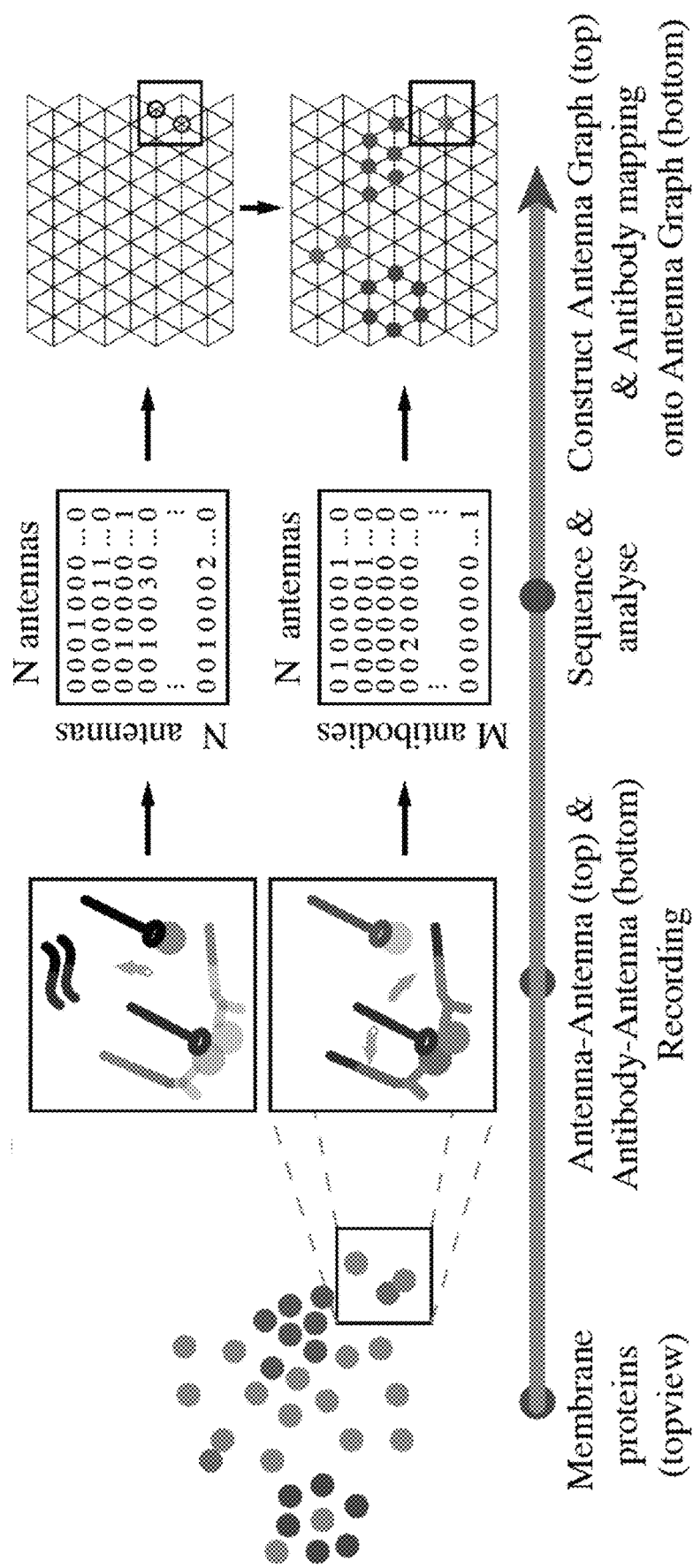

The novel concept presented herein, can be analogized to how a network of cell phone towers can be used to locate a particular mobile phone. The equivalent for cell phone towers are "DNA-antennas", and mobile phones are proteins that are detected. First, to build a DNA antenna network that is dense enough to provide good coverage of the plasma membrane, Applicants can covalently conjugate DNA antennas to the extracellular domain of any membrane protein of a cell, not just the proteins that are desired to be quantified. Once the DNA antenna network is in place, it can be mapped by recording the relative proximities of all antennas in the network. To do so, each DNA antenna carries a "unique antenna identifier" (UAI) sequence. Applicants have designed the antenna to repeatedly produce Reporter DNA molecules (RD) by interacting with nearby antennas. FIG. 1a details the proximity recording mechanism between any two proximal antennas. The RD encodes the UAI's of the two proximal antennas. Crucially, after an RD is produced, each antenna is unmodified, and free to continuously repeat the cycle with other nearby antennas, thus generating a pool of RD's, collectively encoding the connectivity of the antenna network. Sequencing the RD molecules will allow Applicants to reconstruct the relative position of antennas in silico, resulting in an antenna graph where antennas serve as vertices, and the RDs as edges (FIG. 1c, top).

To detect and localize membrane proteins of interest, Applicants can stain cells with antibodies that carry an oligonucleotide that includes a DNA barcode (ABC) that identifies its epitope, and a unique molecular identifier (UMI). The location of an antibody is determined by the identity of the antenna it connects to (FIG. 1b). After the UAI is coupled to ABC, the antenna is free to engage in subsequent proximity recording cycles, but the antibody oligonucleotide is neutralized (i.e. its hybridization sequence is no longer accessible). Antibody oligonucleotides that have coupled to an antenna can be sequenced, enabling bio-informatic projection of proteins onto the antenna graph (FIG. 1c, bottom). The spatial resolution of the antenna graph is dictated by the distance over which DNA proximity recording occurs, and this can be programmed to be 18-40 nm [4], which is on par with current super resolution microscopy approaches. An advantage over microscopy approaches is that Applicants can measure hundreds of antibodies simultaneously as the sequencing readout is not limited by fluorophore spectral overlap. This yields a high dimensional dataset that holds the abundance and relative spatial arrangement of membrane proteins, that Applicants can analyze for significantly occurring spatial patterns over a range of length scales, using for instance multidimensional scaling approaches. The simplest pattern to analyze would be significantly enriched co-localization measured between all the assayed protein targets. Moreover, Applicants can include antibodies targeting ligands to interrogate ligand-receptor interactions, or post-translational modifications, and expand the method beyond antibodies to any biomolecular probe that can be conjugated to an oligonucleotide. The assay can be performed on a commercially available, inducible heterodimerization system, and quantification of the well-validated LPS hand-off by CD14 to TLR4 and TLR4 oligomerization in mouse dendritic cells. Newly discovered nano-scale proteomic patterns can be independently validated by optical super-resolution imaging or expansion microscopy [5].

Significantly, nucleic acid amplification coupled to next generation sequencing enables analysis of many types of scarce biological input material, such as membrane enclosed organelles, exosomes, isolated nuclei, single-cells, or small populations of cells that are biologically or clinically relevant but too rare to provide the input requirements for mass spectrometry. An estimate of the needed sequencing depth indicates that hundreds of proteins with average expression levels could be mapped for hundreds of single cells in a single next-generation-sequencing run. With increased sequencing power, tissues can be analyzed by the methods herein.

The method can map the spatial distribution of membrane proteins, whose interactions are crucial for any signal transduction to or from a cell's environment, and as such underpin important biological processes such as development, differentiation and immunology.

Example 2—Quantifying Intra-Cellular Protein Abundance and Multiway Complex Formation at the Single-Cell Level Quantifying protein pathways at the single-cell level can establish which of all the potential behaviors are physiological and occur within a given cell. Applicants disclose herein an assay that simultaneously measures mRNA and intracellular protein abundance, and protein interactions with other proteins or nucleotides, at the single-cell level in high throughput.

Figure 2A:
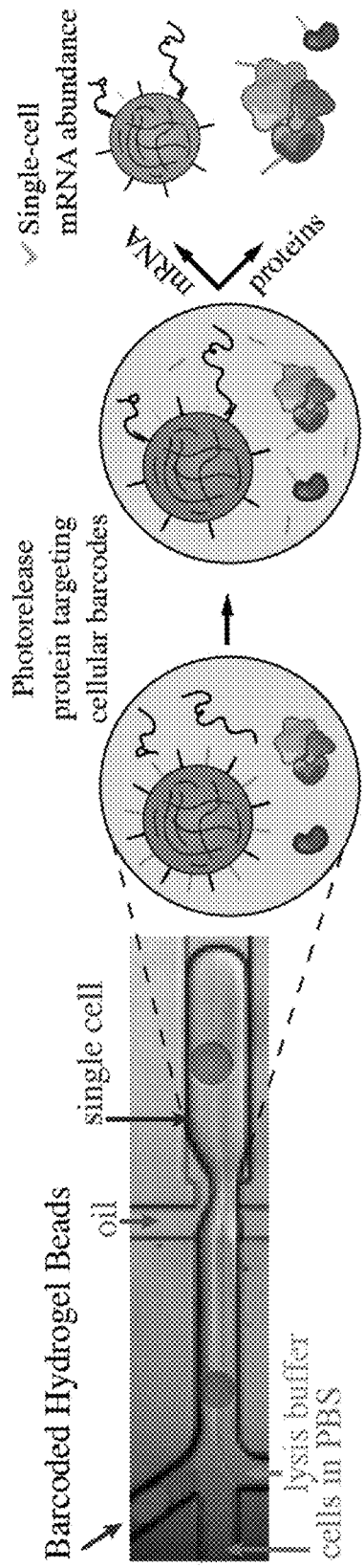
FIG. 2A-FIG. 2D—FIG. 2A shows false-colored brightfield image of microfluidic encapsulation of cells with bifunctional hydrogel beads for simultaneous transcriptomic and proteomic cellular barcoding.

First, to measure mRNA abundance and intracellular protein abundance, Applicant has adapted a microfluidic emulsion droplet assay by co-encapsulating and lysing single cells with hydrogel beads carrying cellular barcode oligonucleotides (FIG. 2a). All oligonucleotides on any given bead share the same cellular barcode, but target either poly adenylated mRNA or proteins. Protein targeting oligonucleotides can be released from the bead by photocleaving, to covalently conjugate to any protein in the droplet (FIG. 2a). After droplet breaking, the hydrogel beads with hybridized mRNA can be separated from the protein lysates for separate processing as described previously [6]. Applicants have purified cellular barcoded proteins, and can subsequently stain with a highly multiplexed panel of DNA barcoded antibodies. A ligation or extension reaction can couple the antibody barcode to the cellular barcode (FIG. 2b), enabling Applicants to determine intracellular protein abundance at the single-cell level and bioinformatically link it to corresponding single-cell transcriptional profile.

Although associating single-cell protein abundance to transcriptomics will greatly advance the ability to measure pathway behavior and link it to transcriptional responses, Applicants can also achieve quantification of protein interactions and protein complex compositions. A compelling example of the type of biological questions to address with this method is the BAF complex pathway-of-assembly, to determine the complex subunit and associated protein factor composition of oncogenic BAF complexes, and define the mechanistic basis of locus-specific and genomewide retargeting of the complex.

Figure 2C:
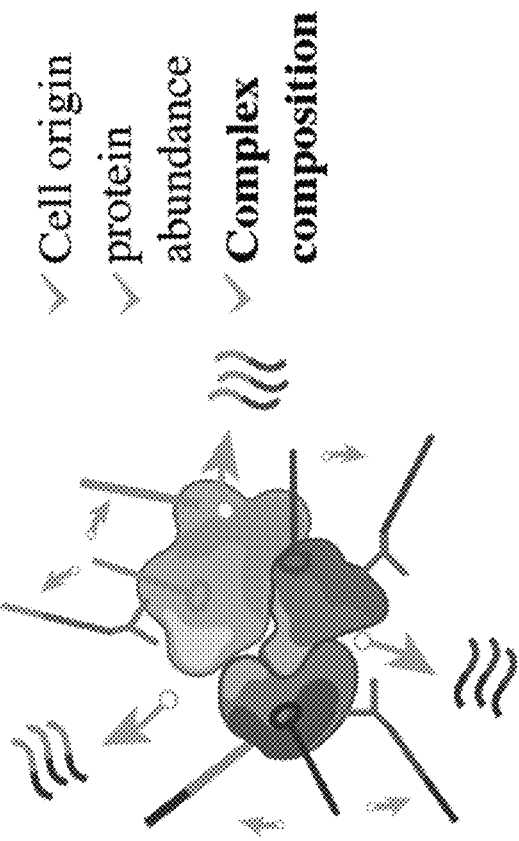
Figure 2B:
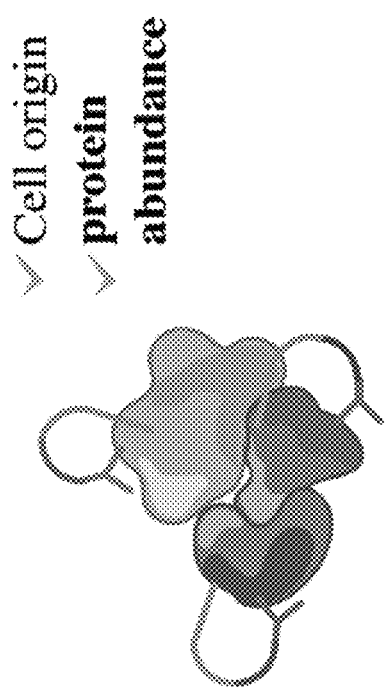

In the method disclosed herein each individual protein complex (or single protein) isolated from the droplets is the basic unit over which a DNA antenna network is built (similar to example 1, where a single cell was the unit). Subsequent staining with DNA barcoded antibodies enables coupling the antibody barcode to the identity of a proximal antenna (as in FIG. 1b), and Applicants can thus assign all the antibodies bound to a given complex to the corresponding antenna network (FIG. 2c). This measures composition of single protein complexes irrespective of the distance between epitopes, a feature particularly of interest for the study of larger protein complexes. Protein complexes isolated from the droplets carry a cellular barcode oligonucleotide that are also designed to register the identity of a nearby antenna, thus allowing for assignment of cellular origin to protein complexes.

Applicants can perform the proximity recording reaction at a dilution that prevents inter-protein complex communication, such that each complex will result in a distinct interconnected set of antennas with corresponding antibody and cellular barcodes in sequencing space, effectively enabling Applicants to quantify individual complexes en masse in a single test tube and thereby obviating the need to (1) microfluidically compartmentalize each individual complex to assign it a unique complex DNA barcode, a process that wastes 90% of input material due to Poisson loading inefficiencies, or (2) build unique complex barcodes by combinatorial indexing methods, which is intractable for a large number of protein complexes in a multiplexed, high throughput experiment. Applicants can validate complex formations by comparing data aggregated over single cells with mass-spectroscopy performed on a population of cells.

Figure 2D:
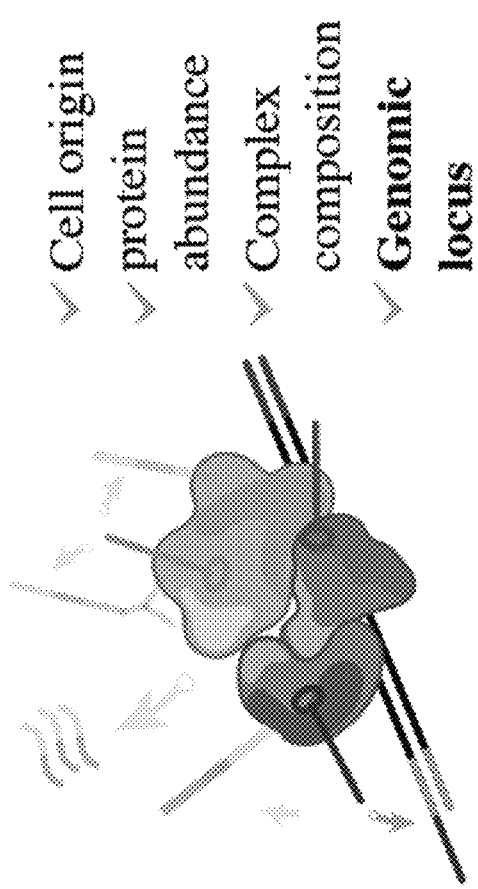

Finally, Applicants can quantify protein-DNA interactions. For instance, fragments of genomic DNA bound to transcription factor or chromatin remodelling complexes can be tagmented, a process that enzymatically cuts DNA and ligates on custom DNA adaptors. Applicants can design the adaptor such that they can connect to the antenna network (FIG. 2d), thus enabling Applicants to quantify protein complex compositions and tie it to the corresponding genomic locus at a genome wide scale. Similarly, Applicants can investigate the composition of protein complexes bound to mRNA by designing probes that hybridize to the antenna network on one end, and to gene specific sequences of mRNA transcripts on the other end. Alternatively, instead of gene specific hybridization sequences, a polyT sequence would target all mRNA molecules.

In conclusion, the methods described herein can enable an unprecedented multi-omic view of the internal state of single cells that stands to increase our understanding of protein pathways behavior and its potential to orchestrate epigenetic and transcriptional responses.

REFERENCES

[1] Stoeckius et al. Simultaneous epitope and transcriptome measurement in single cells. Nature, 201:7, 2017.
[2] Angelo et al. Multiplexed ion beam imaging of human breast tumors. Nature medicine, 20(4):436-442, 2014.
[3] Schapiro et al. histocat: analysis of cell phenotypes and interactions in multiplex image cytometry data. Nature methods, 14(9):873, 2017.
[4] Schaus et al. A dna nanoscope via auto-cycling proximity recording. Nature Communications, 8, 2017.
[5] Chen et al. Expansion microscopy. Science, 347(6221): 543-548, 2015.
[6] Klein et al. Droplet barcoding for single-cell transcriptomics applied to embryonic stem cells. Cell, 161(5): 1187-1201, 2015.

The invention is further described by the following numbered paragraphs:

1. A library of antenna oligonucleotides, each antenna oligonucleotide comprising:
   i. a partially-double-stranded hairpin structure having a loop region and a single stranded 3' end;
   ii. a primer-binding sequence at the 3' end of the hairpin structure;
   iii. a sequence 5' of the primer-binding sequence comprising a unique antenna identifier (UAI) sequence, wherein the UAI sequence is part of or partially part of the single stranded 3' end or is part of the double stranded region, and wherein each antenna has a unique UAI sequence;
   iv. a double-stranded sequence comprising a universal hybridization sequence;
   v. a double-stranded palindromic sequence;
   vi. a modification that terminates polymerization between the palindromic sequence and the loop region of the hairpin; and
   vii. a binding moiety on the loop region for labeling biological modules.
2. The library of paragraph 1, wherein the single stranded sequence comprises a modification before the double stranded region of the hairpin structure that weakens DNA hybridization after primer binding to the primer binding sequence and extension of the primer.
3. The library of paragraph 2, wherein the modification comprises a bulge nucleotide or a phosphorothioate modification.

4. The library of any of paragraphs 1 to 3, wherein the binding moiety comprises a biotin molecule or a Click chemistry moiety.
5. The library of any of paragraphs 1 to 4, wherein the modification that terminates polymerization comprises a non-DNA spacer or an Iso-dC/dG pair.
6. A method of mapping the proximity between biomolecules in discrete biological modules comprising:
   a) modifying a biological sample comprising one or more biological modules with protein linker molecules, wherein the protein linker molecules are linked to proteins in the one or more biological modules;
   b) labeling the modified biological sample with one or more affinity ligands specific for a biomolecule, wherein the one or more affinity ligands are linked to an ABC oligonucleotide comprising an antibody barcode (ABC) specific for each affinity ligand and a universal hybridization sequence;
   c) establishing an antenna network comprising linking antenna oligonucleotides to the protein linker molecules, wherein each antenna oligonucleotide comprises:
      i. a partially-double-stranded hairpin structure having a loop region and a single stranded 3' end,
      ii. a primer-binding sequence at the 3' end of tie hairpin structure,
      iii. a sequence 5' of the primer-binding sequence comprising a unique antenna identifier (UAI) sequence, wherein the UAI sequence is part of or partially part of the single stranded 3' end or is part of the double stranded region, and wherein each antenna has a unique UAI sequence,
      iv. a double-stranded sequence comprising a complementary universal hybridization sequence,
      v. a double-stranded palindromic sequence,
      vi. a modification that terminates polymerization between the palindromic sequence and the loop region of the hairpin, and
      vii. a binding moiety on the loop region capable of being linked to the protein linker molecule; and
   d) incubating the sample with extension reagents and primers complementary to the primer binding sequence under isothermal conditions, wherein the primers are extended to generate a free 3' tail comprising the palindromic sequence and hybridization sequence, whereby the free 3' tail is capable of hybridizing to another antenna oligonucleotide in proximity to generate a reporter molecule comprising two UAIs when extended and whereby the free 3' tail is capable of hybridizing to an ABC oligonucleotide in proximity to generate a UAI-ABC reporter molecule when extended; and
   e) sequencing the oligonucleotides present in the sample, whereby proximity recording to a specific antenna in the network.
7. The method of paragraph 6, wherein the single stranded sequence comprises a modification before the double stranded region of the hairpin structure that weakens DNA hybridization after extension of the primer on the primer binding sequence.
8. The method of paragraph 6, wherein the primer sequence comprises a modification that weakens DNA hybridization after extension of the primer on the primer binding sequence.
9. The method of paragraph 7 or 8, wherein the modification comprises a bulge nucleotide or a phosphorothioate modification.
10. The method of any of paragraphs 6 to 9, wherein the modification that terminates polymerization comprises a non-DNA spacer or an Iso-dC/dG pair.
11. The method of any of paragraphs 6 to 10, wherein the extension reagents comprise a strand displacement polymerase.
12. The method of any of paragraphs 6 to 11, wherein the biological module comprises a protein complex.
13. The method of paragraph 12, wherein the protein complex comprises nucleic acids.
14. The method of paragraph 13, wherein the nucleic acid comprises genomic DNA.
15. The method of any of paragraphs 6 to 11, wherein the biological module comprises a cell, population of cells, organelle, or exosome.
16. The method of paragraph 15, wherein the affinity ligands are specific for membrane proteins.
17. The method of any of paragraphs 6 to 16, wherein the ABC oligonucleotide further comprises a unique molecular identifier (UMI).
18. The method of any of paragraphs 6 to 17, wherein the affinity ligands are antibodies, antibody fragments or aptamers.
19. The method of any of paragraphs 6 to 18, wherein the distance over which DNA proximity occurs is about 6-40 nM.
20. The method of any of paragraphs 6 to 19, wherein the one or more biological modules are fixed.
21. The method of any of paragraphs 6 to 20, wherein the protein linker molecules comprise biotin or click-chemistry moieties.
22. The method of paragraph 21, wherein linking antenna oligonucleotides to the protein linker molecules comprises binding biotin linked antenna oligonucleotides to biotin linker molecules via avidin molecules.
23. The method of paragraph 21, wherein linking antenna oligonucleotides to the protein linker molecules comprises binding antenna oligonucleotides to the linker molecules via click-chemistry.
24. The method of any of paragraphs 6 to 23, wherein before modifying a biological sample the method further comprises tagmentation of genomic DNA present in the biological sample with adaptors configured for hybridizing to the antenna oligonucleotides and extending the UAI sequence, whereby a UAI in proximity to the genomic DNA is transferred to the adaptor.
25. The method of paragraph 24, wherein the one or more affinity ligands comprise affinity ligands specific for histone modifications, whereby chromatin modifications are mapped to genomic loci.
26. The method of any of paragraphs 6 to 25, wherein before modifying a biological sample the method further comprises:
   a) segregating single cells into discrete volumes; and
   b) covalently labeling proteins from single cells with protein labeling oligonucleotides, said oligonucleotides comprising cell of origin barcodes and a sequence configured for hybridizing to the antenna oligonucleotides and extending the UAI sequence, whereby the UAIs in proximity to proteins from a single cell can be identified by sequencing.
27. The method of paragraph 26, wherein the method further comprises tagmentation of genomic DNA in the discrete volumes with adaptors configured for hybridizing to the antenna oligonucleotides and optionally comprising the cell of origin barcode.

28. The method of paragraph 26 or 27, wherein the method further comprises capturing mRNA on capture oligonucleotides in the discrete volumes, said oligonucleotides comprising poly dT, the cell of origin barcodes for the discrete volume, and optionally a UMI.

29. The method of any of paragraphs 26 to 28, wherein the discrete volumes comprise droplets, microfluidic chambers, or microwells.

30. The method of paragraph 29, wherein the discrete volumes are droplets comprising beads labeled with the protein labeling oligonucleotides.

31. The method of paragraph 30, wherein the beads are further labeled with the mRNA capture oligonucleotides.

32. The method of paragraph 30 or 31, wherein the protein labeling oligonucleotides are cleavable.

33. The method of paragraph 31, wherein the mRNA capture oligonucleotides are cleavable.

34. The method of paragraph 32 or 33, wherein the oligonucleotides are chemically-cleavable, enzymatically cleavable, or photocleavable.

35. A system for mapping the proximity between biomolecules in discrete biological modules comprising:
    a) a plurality of antenna oligonucleotides configured for labeling biomolecules, said antenna oligonucleotides comprising:
       i. a partially-double-stranded hairpin structure having a loop region and a single stranded 3' end,
       ii. a primer-binding sequence at the 3' end of the hairpin structure,
       iii. a sequence 5' of the primer-binding sequence comprising a unique antenna identifier (UAI) sequence, wherein the UAI sequence is part of or partially part of the single stranded 3' end or is part of the double stranded region, and wherein each antenna has a unique UAI sequence,
       iv. a double-stranded sequence comprising a universal hybridization sequence,
       v. a double-stranded palindromic sequence,
       vi. a modification that terminates polymerization between the palindromic sequence and the loop region of the hairpin, and
       vii. a binding moiety on the loop region capable of being linked to a protein;
    b) one or more affinity ligands specific for a biomolecule, wherein the one or more affinity ligands are linked to an ABC oligonucleotide comprising an antibody barcode (ABC), wherein each ABC oligonucleotide is configured for hybridizing to the antenna oligonucleotides and extending the UAI sequence;
    c) primers complementary to the primer-binding sequence; and
    d) isothermal extension reagents.

36. The system of paragraph 35, further comprising a transposase loaded with tagmentation adaptors configured for hybridizing to the antenna oligonucleotides and extending the UAI sequence.

37. The system of paragraph 35 or 36, further comprising beads labeled with protein labeling oligonucleotides configured for labeling proteins, said oligonucleotides comprising cell of origin barcodes specific for each bead and a sequence configured for hybridizing to the antenna oligonucleotides and extending the UAI sequence.

38. The system of paragraph 37, wherein the beads are further labeled with mRNA capture oligonucleotides, said oligonucleotides comprising poly dT, the cell of origin barcodes for the bead, and optionally a UMI.

39. The system of paragraph 37 or 38, wherein the protein labeling oligonucleotides are cleavable.

40. The system of paragraph 38, wherein the mRNA capture oligonucleotides are cleavable.

41. The system of paragraph 39 or 40, wherein the oligonucleotides are chemically-cleavable, enzymatically cleavable, or photocleavable.

42. A method of measuring proteins in single cells comprising:
    a) segregating single cells into discrete volumes;
    b) covalently labeling proteins from the single cells with protein labeling oligonucleotides, said oligonucleotides comprising cell of origin barcodes;
    c) optionally, pooling the discrete volumes;
    d) labeling the proteins with one or more affinity ligands each specific for a target protein, wherein the one or more affinity ligands are linked to an ABC oligonucleotide comprising an antibody barcode (ABC) specific for the target protein, wherein each ABC oligonucleotide is configured for hybridizing to the protein labeling oligonucleotides and extending the cell of origin barcodes;
    e) incubating the sample with extension reagents under isothermal conditions; and
    f) sequencing the extended ABC oligonucleotides present in the sample, thereby identifying proteins in single cells.

43. The method of paragraph 42, wherein the method further comprises capturing mRNA on capture oligonucleotides comprising poly dT, the cell of origin barcodes for the discrete volume, and optionally a UMI.

44. The method of paragraph 42 or 43, wherein the discrete volumes comprise droplets, microfluidic chambers, or microwells.

45. The method of paragraph 44, wherein the discrete volumes are droplets comprising beads labeled with the protein labeling oligonucleotides.

46. The method of paragraph 45, wherein the protein labeling oligonucleotides are cleavable.

47. The method of paragraph 45 or 46, wherein the beads are further labeled with the mRNA capture oligonucleotides.

48. The method of paragraph 47, wherein the mRNA capture oligonucleotides are cleavable.

49. An oligonucleotide-labeled bead for analyzing proteins expressed in single cells, wherein said bead comprises a plurality of first oligonucleotides, wherein each of said first oligonucleotides comprises:
    a. a cleavable linker directly attached to the bead;
    b. a protein linking moiety;
    c. a cell barcode sequence, wherein the cell barcode sequence is the same across all oligonucleotides on said bead, but varies among the oligonucleotides on any other individual bead; and
    d. a universal hybridization sequence.

50. The oligonucleotide-labeled bead of paragraph 49, wherein the linker is chemically-cleavable, enzymatically cleavable, or photocleavable.

51. The oligonucleotide-labeled bead of paragraph 49 or 50, wherein the protein linking moiety is a photoreactive group configured to covalently link to proteins upon experimentally defined illumination.

52. The oligonucleotide-labeled bead of paragraph 49 or 50, wherein the protein linking moiety is a click chemistry group configured to covalently link to proteins.

53. The oligonucleotide-labeled bead of any of paragraphs 49 to 52, further comprising a plurality of second oligonucleotides on said bead, said second oligonucleotides comprising:
   a. a linker directly attached to the bead;
   b. the cell barcode sequence; and
   c. an oligonucleotide redundant sequence for capturing polyadenylated mRNAs and priming reverse transcription.

54. The oligonucleotide-labeled bead of paragraph 53, wherein the oligonucleotide sequence for capturing polyadenylated mRNAs and priming reverse transcription is an oligo dT sequence.

55. The oligonucleotide-labeled bead of paragraph 53 or 54, wherein each second oligonucleotide comprises a Unique Molecular Identifier (UMI).

56. The oligonucleotide-labeled bead of any of paragraphs 53 to 55, wherein the second oligonucleotide linker is chemically-cleavable, enzymatically cleavable, or photocleavable.

57. The oligonucleotide-labeled bead of paragraph 56, wherein the second oligonucleotide linker is differentially cleavable as compared to the first oligonucleotide linker, whereby each linker is capable of cleavage at experimentally defined times.

58. The oligonucleotide-labeled bead of any of paragraphs 53 to 57, wherein the second oligonucleotides comprise 1-5% of oligonucleotides on said bead and the oligonucleotides for protein linking comprise 95-99% of oligonucleotides on said bead.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed:

1. A library of antenna oligonucleotides, each antenna oligonucleotide comprising:
   i) a partially-double-stranded hairpin structure having a loop region and a single stranded 3' end;
   ii) a primer-binding sequence at the 3' end of the hairpin structure;
   iii) a sequence 5' of the primer-binding sequence comprising a unique antenna identifier (UAI) sequence, wherein the UAI sequence is part of or partially part of the single stranded 3' end or is part of the double stranded region, and wherein each antenna has a unique UAI sequence as compared to any other antenna oligonucleotide in the library;
   iv) a double-stranded sequence 5' of the UAI comprising a universal hybridization sequence that is the same for all of the antenna oligonucleotides in the library;
   v) a double-stranded palindromic sequence of at least 4 nucleotides 5' of the universal hybridization sequence;
   vi) a modification between the palindromic sequence and the loop region of the hairpin on the 3' side of the loop that terminates polymerization primed from the primer binding sequence at the 3' end of the hairpin structure; and
   vii) a binding moiety on the loop region for labeling biological modules.

2. The library of claim 1, wherein the single stranded sequence comprises a modification before the double stranded region of the hairpin structure that weakens DNA hybridization after primer binding to the primer binding sequence and extension of the primer, optionally, wherein the modification comprises a bulge nucleotide or a phosphorothioate modification;
   wherein the binding moiety comprises a biotin molecule or a Click chemistry moiety; and/or
   wherein the modification that terminates polymerization comprises a non-DNA spacer or an Iso-dC/dG pair.

3. A method of establishing an antenna network in discrete biological modules comprising linking a library of antenna oligonucleotides to proteins in one ore more biological modules, wherein the one or more biological modules are optionally fixed,
   wherein each antenna oligonucleotide comprises:
   i) a partially-double-stranded hairpin structure having a loop region and a single stranded 3' end;
   ii) a primer-binding sequence at the 3' end of the hairpin structure;
   iii) a sequence 5' of the primer-binding sequence comprising a unique antenna identifier (UAI) sequence, wherein the UAI sequence is part of or partially part of the single stranded 3' end or is part of the double stranded region, and wherein each antenna has a unique UAI sequence as compared to any other antenna oligonucleotide in the library;
   iv) a double-stranded sequence 5' of the UAI comprising a universal hybridization sequence that is the same for all of the antenna oligonucleotides in the library;
   v) a double-stranded palindromic sequence of at least 4 nucleotides 5' of the universal hybridization sequence;
   vi) a modification between the palindromic sequence and the loop region of the hairpin on the 3' side of the loop that terminates polymerization primed from the primer binding sequence at the 3' end of the hairpin structure; and
   vii) a binding moiety on the loop region for labeling biological modules.

4. The method of claim 3, wherein the single stranded sequence comprises a modification before the double stranded region of the hairpin structure that weakens DNA hybridization after extension of the primer on the primer binding sequence, optionally, wherein the modification comprises a bulge nucleotide or a phosphorothioate modification.

5. The method of claim 3, wherein the modification that terminates polymerization comprises a non-DNA spacer or an Iso-dC/dG pair.

6. The method of claim 3, wherein the one or more biological modules comprise a protein complex, optionally, wherein the protein complex comprises nucleic acids, optionally, wherein the nucleic acids comprise genomic DNA; or
wherein the one or more biological modules comprise a cell, population of cells, organelle, or exosome.

7. The method of claim 3, wherein linking a library of antenna oligonucleotides to proteins in one or more biological modules is via protein linker molecules linked to proteins in the one or more biological modules, and wherein the protein linker molecules comprise biotin or click-chemistry moieties, optionally, wherein linking antenna oligonucleotides to the protein linker molecules comprises binding biotin linked antenna oligonucleotides to biotin linker molecules via avidin molecules or binding antenna oligonucleotides to the linker molecules via click-chemistry.

8. The method of claim 3, wherein the biological modules are further labeled with one or more affinity ligands specific for a biomolecule, wherein the one or more affinity ligands are linked to an ABC oligonucleotide comprising an antibody barcode (ABC) that identifies the biomolecule the affinity ligand is specific for and a universal hybridization sequence complementary with the universal hybridization sequence of the antenna library; and/or
wherein the biological modules are further modified by tagmentation of genomic DNA present in the biological modules with adaptors comprising a universal hybridization sequence complementary with the universal hybridization sequence of the antenna library.

9. The method of claim 8, wherein the one or more affinity ligands comprise affinity ligands specific for histone modifications, whereby chromatin modifications are mapped to genomic loci.

10. The method of claim 3, wherein before establishing an antenna network the method further comprises:
a) segregating single cells into discrete volumes; and
b) covalently labeling proteins from single cells with protein labeling oligonucleotides, said oligonucleotides comprising cell of origin barcodes and a universal hybridization sequence complementary with the universal hybridization sequence of the antenna library.

11. The method of claim 10, wherein the method further comprises tagmentation of genomic DNA in the discrete volumes with adaptors comprising a universal hybridization sequence complementary with the universal hybridization sequence of the antenna library, optionally comprising the cell of origin barcode.

12. The method of claim 10, wherein the method further comprises capturing mRNA on capture oligonucleotides in the discrete volumes, said oligonucleotides comprising poly dT, the cell of origin barcodes for the discrete volume, and optionally a UMI.

13. The method of claim 10, wherein the discrete volumes comprise droplets, microfluidic chambers, or microwells, optionally, wherein the discrete volumes are droplets comprising beads labeled with the protein labeling oligonucleotides, optionally, wherein the beads are further labeled with the mRNA capture oligonucleotides.

14. The method of claim 13, wherein the protein labeling oligonucleotides are cleavable; and/or wherein the mRNA capture oligonucleotides are cleavable, optionally, wherein the oligonucleotides are chemically-cleavable, enzymatically cleavable, or photocleavable.

15. A system for mapping the proximity between biomolecules in discrete biological modules comprising:
a) a library of antenna oligonucleotides according to claim 1 configured for labeling biomolecules, wherein the binding moiety on the loop region is capable of being linked to a protein;
b) one or more affinity ligands specific for a biomolecule, wherein the one or more affinity ligands are linked to an ABC oligonucleotide comprising an antibody barcode (ABC) that identifies the biomolecule the affinity ligand is specific for and a universal hybridization sequence complementary with the universal hybridization sequence of the antenna library;
c) primers complementary to the primer-binding sequence of the antenna library; and
d) isothermal extension reagents.

16. The system of claim 15, further comprising a transposase loaded with tagmentation adaptors comprising a universal hybridization sequence complementary with the universal hybridization sequence of the antenna library.

17. The system of claim 15, further comprising beads labeled with protein labeling oligonucleotides configured for labeling proteins, said oligonucleotides comprising a protein linking moiety, a cell of origin barcode specific for each bead, and a universal hybridization sequence complementary with the universal hybridization sequence of the antenna library, optionally, wherein the beads are further labeled with mRNA capture oligonucleotides, said oligonucleotides comprising poly dT, the cell of origin barcodes for the bead, and optionally a UMI, optionally, wherein the protein labeling oligonucleotides are cleavable; and/or wherein the mRNA capture oligonucleotides are cleavable, optionally, wherein the oligonucleotides are chemically-cleavable, enzymatically cleavable, or photocleavable.

18. An oligonucleotide-labeled bead for analyzing proteins expressed in single cells, wherein said bead comprises a plurality of first oligonucleotides, wherein each of said first oligonucleotides comprises:
a) a cleavable linker directly attached to the bead;
b) a protein linking moiety, wherein the protein linking moiety is a photoreactive group configured to covalently link to proteins upon experimentally defined illumination or is a click chemistry group configured to covalently link to proteins;
c) a cell barcode sequence, wherein the cell barcode sequence is the same across all oligonucleotides on said bead, but varies among the oligonucleotides on any other individual bead; and
d) a universal hybridization sequence.

19. The oligonucleotide-labeled bead of claim 18, wherein the linker is chemically-cleavable, enzymatically cleavable, or photocleavable.

20. The oligonucleotide-labeled bead of claim 18, further comprising a plurality of second oligonucleotides on said bead, said second oligonucleotides comprising:
a) a linker directly attached to the bead;
b) the cell barcode sequence; and
c) an oligonucleotide redundant sequence for capturing polyadenylated mRNAs and priming reverse transcription.

21. The oligonucleotide-labeled bead of claim 20, wherein the oligonucleotide sequence for capturing polyadenylated mRNAs and priming reverse transcription is an oligo dT sequence;
wherein each second oligonucleotide comprises a Unique Molecular Identifier (UMI);
wherein the second oligonucleotide linker is chemically-cleavable, enzymatically cleavable, or photocleavable, optionally, wherein the second oligonucleotide linker is differentially cleavable as compared to the first oligonucleotide linker, whereby each linker is capable of cleavage at experimentally defined times; and/or wherein the second oligonucleotides comprise 1-5% of oligonucleotides on said bead and the oligonucleotides for protein linking comprise 95-99% of oligonucleotides on said bead.

22. The method of claim 3, further comprising:
a) incubating the biological modules having an established antenna network with extension reagents and primers complementary to the primer binding sequence on the antenna network under isothermal conditions; and
b) sequencing the reporter molecules generated to locate the positions of the antenna oligonucleotides on the antenna network.

23. The method of claim 22, wherein the primer binding sequence comprises a modification that weakens DNA hybridization after extension of the primer on the primer binding sequence, optionally, wherein the modification comprises a bulge nucleotide or a phosphorothioate modification; and/or wherein the extension reagents comprise a strand displacement polymerase.

24. The method of claim 8, further comprising:
a) incubating the biological modules having an established antenna network with extension reagents and primers complementary to the primer binding sequence on the antenna network under isothermal conditions; and
b) sequencing the reporter molecules generated to locate the positions of the antenna oligonucleotides and biomolecules on the antenna network.

25. The method of claim 24, wherein the primer binding sequence comprises a modification that weakens DNA hybridization after extension of the primer on the primer binding sequence, optionally, wherein the modification comprises a bulge nucleotide or a phosphorothioate modification; and/or wherein the extension reagents comprise a strand displacement polymerase.

26. The method of claim 8, wherein the ABC oligonucleotide further comprises a unique molecular identifier (UMI); and/or wherein the affinity ligands are antibodies, antibody fragments or aptamers; and/or wherein the affinity ligands are specific for membrane proteins; and/or wherein the distance over which DNA proximity occurs is about 6-40 nM; and/or wherein the one or more biological modules are fixed.

* * * * *